(12) United States Patent
Caffey et al.

(10) Patent No.: US 8,920,376 B2
(45) Date of Patent: Dec. 30, 2014

(54) FILL-STATUS SENSORS FOR DRUG PUMP DEVICES

(75) Inventors: Sean Caffey, Hawthorne, CA (US);
Po-Ying Li, Monrovia, CA (US);
Yu-Chong Tai, Pasadena, CA (US);
Jeffrey Brennan, Los Angeles, CA (US)

(73) Assignee: MiniPumps, LLC, Pasadena, CA (US)

( * ) Notice: Subject to any disclaimer, the term of this patent is extended or adjusted under 35 U.S.C. 154(b) by 305 days.

(21) Appl. No.: 13/091,031

(22) Filed: Apr. 20, 2011

(65) Prior Publication Data

US 2011/0270188 A1 Nov. 3, 2011

Related U.S. Application Data

(60) Provisional application No. 61/326,047, filed on Apr. 20, 2010, provisional application No. 61/367,686, filed on Jul. 26, 2010, provisional application No. 61/423,945, filed on Dec. 16, 2010, provisional application No. 61/449,899, filed on Mar. 7, 2011.

(51) Int. Cl.
*A61M 37/00* (2006.01)
*A61M 5/145* (2006.01)
*A61M 5/142* (2006.01)
*A61M 5/168* (2006.01)

(52) U.S. Cl.
CPC ....... *A61M 5/14526* (2013.01); *A61M 5/14593* (2013.01); *A61M 5/14248* (2013.01); *A61M 5/14276* (2013.01); *A61M 5/1684* (2013.01); *A61M 5/16886* (2013.01); *A61M 2005/14204* (2013.01); *A61M 2205/3523* (2013.01); *A61M 2205/3569* (2013.01); *A61M 2205/3584* (2013.01); *A61M 2205/3592* (2013.01); *A61M 2210/0612* (2013.01)

USPC ........... 604/141; 604/114; 604/131; 604/135; 604/140; 604/143; 604/152; 604/158; 604/173; 604/21; 604/65; 604/891.1; 604/892.1; 204/630

(58) Field of Classification Search
USPC .......... 203/630; 604/114, 131, 135, 140, 141, 604/143, 152, 158, 173, 21, 65, 891.1, 604/892.1
See application file for complete search history.

(56) References Cited

U.S. PATENT DOCUMENTS 2,445,477 A * 7/1948 Folkman .................. 206/221
3,175,558 A * 3/1965 Caillonette et al. ........... 607/114
4,203,441 A * 5/1980 Theeuwes .................. 604/892.1

(Continued)

FOREIGN PATENT DOCUMENTS

DE 2004-036358 2/2006
GB 1345764 2/1974

(Continued)

OTHER PUBLICATIONS

Invitation to Pay Additional Fees and Partial Search Report mailed Aug. 4, 2011 for International Application No. PCT/US2011/033329 (5 pages).

(Continued)

*Primary Examiner* — Scott Medway
(74) *Attorney, Agent, or Firm* — Morgan, Lewis & Bockius LLP

(57) ABSTRACT

The filling status of a drug reservoir in a drug pump devices may be determined with mechanical and/or magnetic position sensor associated with a reservoir boundary.

3 Claims, 15 Drawing Sheets

(56) References Cited

U.S. PATENT DOCUMENTS

| | | | |
|---|---|---|---|
| 4,237,881 A * | 12/1980 | Beigler et al. | 604/141 |
| 4,886,499 A | 12/1989 | Cirelli et al. | |
| 4,969,874 A | 11/1990 | Michel et al. | |
| 5,062,834 A * | 11/1991 | Gross et al. | 604/143 |
| 5,090,963 A * | 2/1992 | Gross et al. | 604/132 |
| 5,163,909 A * | 11/1992 | Stewart | 604/140 |
| 5,242,406 A * | 9/1993 | Gross et al. | 604/132 |
| 5,279,607 A * | 1/1994 | Schentag et al. | 604/890.1 |
| 5,318,557 A | 6/1994 | Gross | |
| 5,354,264 A | 10/1994 | Bae et al. | |
| 5,368,571 A * | 11/1994 | Horres, Jr. | 604/131 |
| 5,399,166 A * | 3/1995 | Laing | 604/146 |
| 5,425,716 A * | 6/1995 | Kawasaki et al. | 604/152 |
| 5,458,095 A * | 10/1995 | Post et al. | 123/3 |
| 5,527,288 A | 6/1996 | Gross et al. | |
| 5,553,741 A * | 9/1996 | Sancoff et al. | 222/1 |
| 5,616,219 A * | 4/1997 | Patterson | 204/241 |
| 5,707,499 A * | 1/1998 | Joshi et al. | 204/230.5 |
| 5,713,857 A * | 2/1998 | Grimard et al. | 604/82 |
| 5,725,017 A | 3/1998 | Elsberry et al. | |
| 5,741,275 A | 4/1998 | Wyssmann | |
| 5,785,688 A | 7/1998 | Joshi et al. | |
| 5,951,538 A * | 9/1999 | Joshi et al. | 604/500 |
| 6,048,328 A * | 4/2000 | Haller et al. | 604/288.03 |
| 6,254,586 B1 * | 7/2001 | Mann et al. | 604/506 |
| 6,370,970 B1 * | 4/2002 | Hosokawa et al. | 73/862.56 |
| 6,458,102 B1 | 10/2002 | Mann et al. | |
| 6,520,936 B1 * | 2/2003 | Mann | 604/141 |
| 6,697,694 B2 * | 2/2004 | Mogensen | 700/119 |
| 6,817,252 B2 * | 11/2004 | Wiklund et al. | 73/861.44 |
| 6,955,670 B2 * | 10/2005 | Martin et al. | 604/891.1 |
| 7,429,258 B2 | 9/2008 | Angel et al. | |
| 7,470,267 B2 | 12/2008 | Joshi et al. | |
| 7,517,440 B2 * | 4/2009 | Anex et al. | 204/450 |
| 7,524,304 B2 | 4/2009 | Genosar | |
| 7,766,873 B2 * | 8/2010 | Moberg et al. | 604/131 |
| 7,887,508 B2 | 2/2011 | Meng et al. | |
| 8,147,447 B2 * | 4/2012 | Sundar et al. | 604/67 |
| 2002/0016569 A1 * | 2/2002 | Critchlow et al. | 604/131 |
| 2003/0014014 A1 | 1/2003 | Nitzan | |
| 2004/0126253 A1 | 7/2004 | Gray et al. | |
| 2005/0010175 A1 * | 1/2005 | Beedon et al. | 604/218 |
| 2005/0076242 A1 | 4/2005 | Breuer | |
| 2005/0209562 A1 * | 9/2005 | Kim | 604/141 |
| 2005/0214129 A1 * | 9/2005 | Greene et al. | 417/18 |
| 2006/0047538 A1 | 3/2006 | Condurso et al. | |
| 2006/0052666 A1 * | 3/2006 | Kumar et al. | 600/159 |
| 2006/0116641 A1 * | 6/2006 | Gordon et al. | 604/141 |
| 2007/0060870 A1 | 3/2007 | Tolle et al. | |
| 2007/0066939 A1 | 3/2007 | Krulevitch et al. | |
| 2007/0191770 A1 * | 8/2007 | Moberg et al. | 604/131 |
| 2007/0255250 A1 | 11/2007 | Moberg et al. | |
| 2007/0275384 A1 | 11/2007 | Leppert et al. | |
| 2008/0015494 A1 | 1/2008 | Santini, Jr. et al. | |
| 2008/0022789 A1 * | 1/2008 | Okuno et al. | 73/866.5 |
| 2008/0033255 A1 | 2/2008 | Essenpreis et al. | |
| 2008/0312584 A1 | 12/2008 | Montgomery et al. | |
| 2009/0205399 A1 * | 8/2009 | Sun et al. | 73/1.02 |
| 2009/0227855 A1 | 9/2009 | Hill et al. | |
| 2009/0234594 A1 * | 9/2009 | Carlisle et al. | 702/49 |
| 2009/0281528 A1 * | 11/2009 | Grovender et al. | 604/892.1 |
| 2009/0306585 A1 * | 12/2009 | Pang et al. | 604/67 |
| 2009/0308752 A1 | 12/2009 | Evans et al. | |
| 2010/0222769 A1 * | 9/2010 | Meng et al. | 604/891.1 |
| 2010/0234805 A1 | 9/2010 | Kaufmann et al. | |
| 2010/0241103 A1 | 9/2010 | Kraft et al. | |
| 2010/0292635 A1 * | 11/2010 | Sundar | 604/67 |
| 2011/0144586 A1 | 6/2011 | Michaud et al. | |
| 2011/0184342 A1 | 7/2011 | Pesach et al. | |
| 2011/0202032 A1 * | 8/2011 | Shih et al. | 604/500 |
| 2012/0222488 A1 * | 9/2012 | Slocum | 73/715 |

FOREIGN PATENT DOCUMENTS

| | | |
|---|---|---|
| GB | 1452104 | 10/1976 |
| WO | WO-00/072900 | 12/2000 |
| WO | WO-00/74751 | 12/2000 |
| WO | WO-01/66173 | 9/2001 |
| WO | WO-2004/026281 | 4/2004 |
| WO | WO-2005/034814 | 4/2005 |
| WO | WO-2007/125456 | 11/2007 |
| WO | WO-2009/015389 | 1/2009 |
| WO | WO-2011/025913 | 3/2011 |

OTHER PUBLICATIONS

International Search Report and Written Opinion mailed Nov. 23, 2011 for International Application No. PCT/US2011/033329 (17 pages).

Examination Report mailed Jan. 29, 2009 for European Patent Application No. 07753177.0 (6 pages).

Examination Report mailed Feb. 5, 2010 for European Patent Application No. 07753177.0 (3 pages).

Extended Search Report mailed Dec. 15, 2011 for European Patent Application No. 11153615.7 (9 pages).

Extended Search Report mailed Dec. 12, 2011 for European Patent Application No. 11153618.1 (10 pages).

* cited by examiner

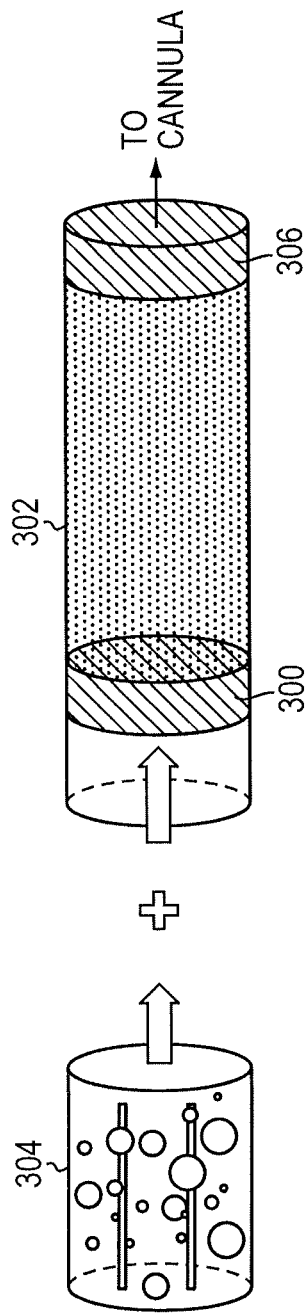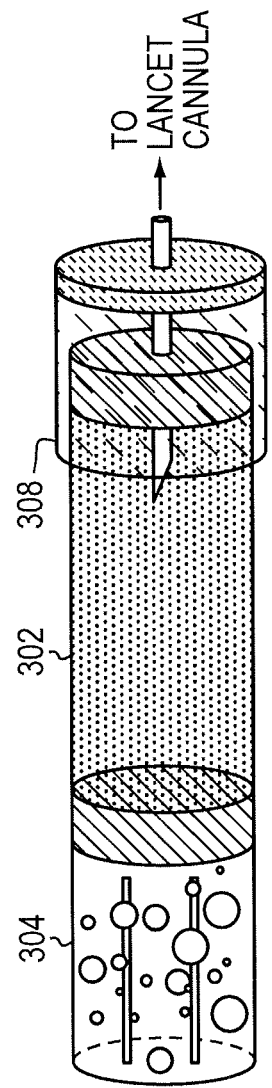

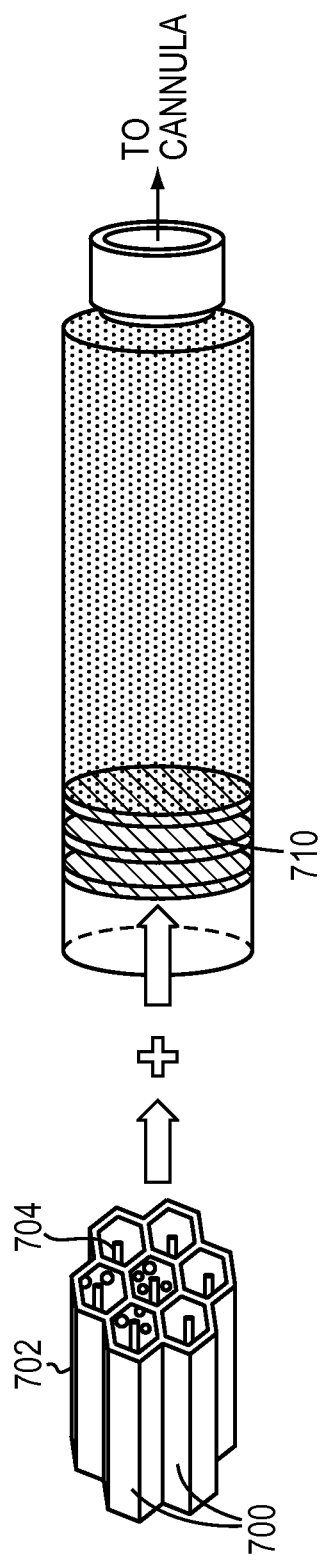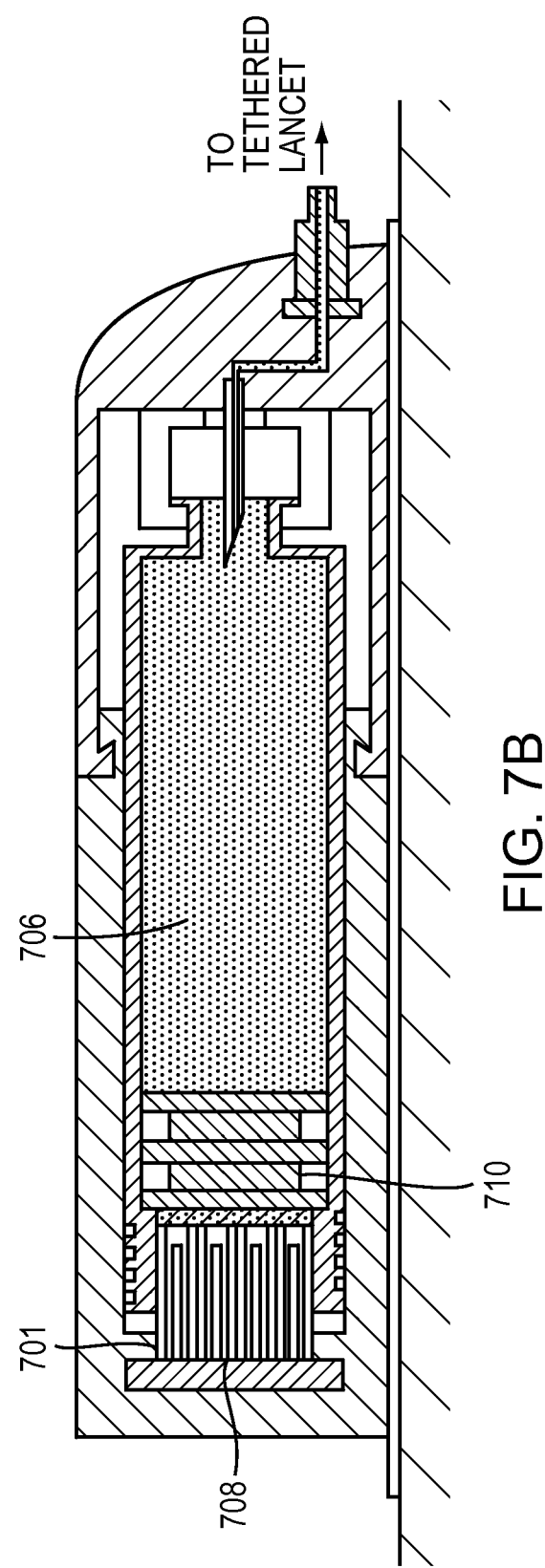

FILL-STATUS SENSORS FOR DRUG PUMP DEVICES

CROSS-REFERENCE TO RELATED APPLICATIONS

This application claims priority to and the benefit of, and incorporates herein by reference in its entirety, U.S. Provisional Patent Applications No. 61/326,047, filed on Apr. 20, 2010, No. 61/367,686, filed on Jul. 26, 2010, No. 61/423,945, filed on Dec. 16, 2010, and No. 61/449,899, filed on Mar. 7, 2011.

TECHNICAL FIELD

The invention relates, generally, to drug pump devices, and, in particular, to systems and methods for determining the filling status of drug reservoirs in such devices.

BACKGROUND

As patients live longer and are diagnosed with chronic and often debilitating ailments, there is an increased need for improvements to the speed, convenience, and efficacy of drug delivery. For example, many chronic conditions, including multiple sclerosis, diabetes, osteoporosis, and Alzheimer's disease, are incurable and difficult to treat with currently available therapies: oral medications have systemic side effects; injections may require a medical visit, can be painful, and risk infection; and sustained-release implants must typically be removed after their supply is exhausted, and offer limited ability to change the dose in response to the clinical picture. In recent decades, several types of wearable drug delivery devices have been developed, including battery-powered miniature pumps, implantable drug dispensers, and diffusion-mediated skin patches.

Treatments for a number of chronic diseases currently require subcutaneous administration of a drug or therapeutic agent either continuously or at specific times or time intervals in highly controlled doses. Subcutaneous injections take advantage of the lack of blood flow to the subcutaneous layer, which allows the administered drug to be absorbed more slowly over a longer period of time (compared with direct injection into the bloodstream). Additional advantages to subcutaneous delivery of some drugs (i.e., vaccines, tuberculin tests, immunostimulants, etc.) to the tissue region are the targeting of lymph tissue and lymphatic drainage for subsequent antigen presentation to the body. Traditionally, these types of injections have been administered either by the patient or a medical practitioner anywhere from several times a day to once every few weeks. Such frequent injections can result in discomfort, pain, and inconvenience to the patient. Self-administration further poses the risk of non-compliance or errors in dosage events.

These problems can be at least partially overcome by wearable, electronically controlled drug pump devices capable of delivering highly controlled dosages of drug continuously or intermittently, depending on the needs of the patient. Such pump devices may be programmed to deliver drug in accordance with specified delivery protocols for extended periods of time, which can, in some circumstances, virtually eliminate the need for human control of pump operation. Of course, once the drug reservoir of a pump device is empty, human intervention is necessary to replace or refill the device. To avoid unexpected depletion of the drug reservoir and minimize the interruption of drug delivery to the patient, it would therefore be desirable to equip the pump device with features for detecting the filling status of the reservoir and alerting the patient or clinician when the drug is nearly used up.

SUMMARY

The present invention provides, in various embodiments, drug pump devices with filling status sensors. The pump devices generally include a displaceable member, such as a piston or diaphragm, that moves inside the drug reservoir so as to expel drug from the reservoir for delivery to an infusion site. Sensors associated with the displaceable member and/or the reservoir may be employed to determine the position of the displaceable member relative to the reservoir, which allows the amount of drug remaining in the reservoir to be inferred. For example, in certain diaphragm pump embodiments, a magnet is attached to the diaphragm, and an induction coil placed at or near a wall of the reservoir may detect the movement of the magnet and determine the position of the diaphragm based thereon. Similarly, in piston pump devices, a magnet or optical reflector associated with the piston may be used, in combination with induction coils, Hall effect sensors, and/or LEDs and optical sensors placed adjacent the drug reservoir, to measure the piston position. The position need not be determined precisely; rather, it may suffice to sense piston motion past a number of discrete threshold positions. In one inexpensive embodiment, such discrete piston positions are mechanically sensed, e.g., based on the breakage of strings of different lengths tied to the piston.

In a first aspect, the invention provides a drug pump device comprising a vial that includes a drug reservoir therein, a piston movably disposed inside the vial and facing the reservoir with one side, a pump (e.g., an electrolysis pump) for applying pressure to the other side of the piston so as to move the piston to cause drug delivery from the reservoir, and a sensor for mechanically measuring a position of the piston inside the vial. The mechanical sensor may include strings of different lengths connecting the piston to an opposed wall of the pump. The lengths of the strings may be selected such that the strings successively break as the piston reaches successive specified positions inside the vial. The strings may include or consist essentially of nylon and/or a metal. In the case of metal strings, the strings may form part of electronic circuits, and breakage of strings may cause the circuits to generate an electronic signal. Alternatively, the vial may transparent, rendering breakage of the wires observable by eye. The device may further include a fill state indicator for causing an alert when the piston has moved by a predetermined distance.

In another aspect, the invention is directed to a drug pump device including a vial with a drug reservoir therein, a piston movably disposed inside the vial (with a first side of the piston facing the drug reservoir), a pump for applying pressure to a second side of the piston so as to move the piston to cause drug delivery from the reservoir, and a sensor for capacitively measuring a position of the piston inside the vial. The piston may include or consist of a material whose dielectric properties (e.g., its dielectric constant or dielectric loss factor) differ substantially from dielectric properties of a drug in the vial. For example, in some embodiments, the dielectric constants of the piston and drug differ by more than 20%, in some by more than 50%, and in some by more than a factor of two.

In another aspect, the invention is directed to a drug pump device including an electrolysis chamber formed between an adhesive patch and an expandable diaphragm, a drug reservoir formed between the diaphragm and a dome disposed above the diaphragm, a magnet associated with the diaphragm, and a sensor (e.g., an induction coil) associated with the dome for determining a relative distance between the magnet and a top of the dome. Generation of gas within the electrolysis chamber applies pressure to the diaphragm to force liquid from the drug reservoir. The device may have a controller responsive to the sensor for controlling a rate of electrolysis based on the determined distance. Further, the device may include a fill state indicator for causing an alert when a predetermined threshold distance between the magnet and the top of the dome is reached.

A further aspect is directed to a drug pump device that includes an electrolysis pump chamber and a secondary pump chamber located adjacent one another and connected by a fluid path including a valve. The electrolysis pump chamber is formed in an enclosure having an expandable portion (e.g., a flexible diaphragm). The upper surface of the secondary chamber is formed by a (second) flexible diaphragm, and a drug reservoir is formed between the flexible diaphragm and a dome disposed thereabove. When the valve is in a closed state, it prevents fluid communication between the electrolysis and secondary pump chambers, thereby facilitating pressure buildup in the electrolysis pump chamber due to gas generation therein. When the valve is in an open state, it allows fluid communication between the electrolysis and secondary pump chambers, and thus facilitates pressure release from the electrolysis pump chamber to the secondary pump chamber, which causes drug to be expelled from the reservoir. The device may further include a pressure sensor inside the electrolysis chamber, which may gauge when the electrolysis needs to be turned on to build up pressure inside the electrolysis pump chamber.

As used herein, the term "substantially" means±10% and, in some embodiments, ±5%.

BRIEF DESCRIPTION OF THE DRAWINGS

The foregoing and the following detailed description of the invention may be more readily understood in conjunction with the drawings, in which:

FIGS. 3A and 3B illustrate, in isometric views, the assembly of a piston pump device with a hydrogel-based electrolysis pump in accordance one embodiment;

FIGS. 7A and 7B are schematic isometric and side views, respectively, of a piston pump device with a honeycomb electrode structure in accordance with one embodiment;

DETAILED DESCRIPTION

Figure 1:
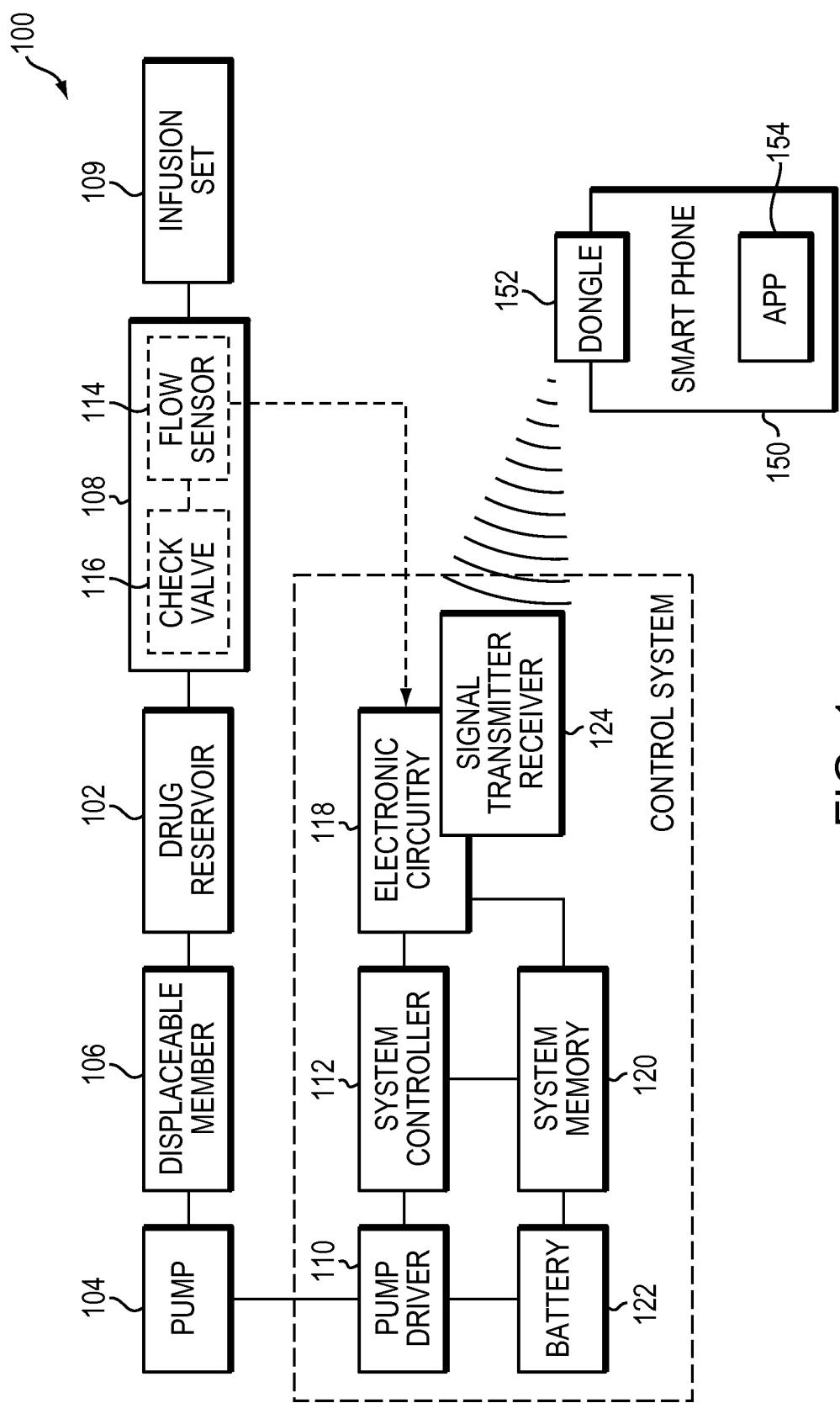
FIG. 1 is a block diagram illustrating the functional components of drug pump devices in accordance with various embodiments.

FIG. 1 illustrates, in block diagram form, the components of a drug pump device 100 in accordance with various embodiments of the present invention. In general, the pump device 100 includes a drug reservoir 102 that interfaces with a pump 104 via a displaceable member 106. The displaceable member 106 may be, for example, a piston, diaphragm, bladder, or plunger. In use, the drug reservoir 102 is filled with medication in liquid form, and pressure generated by the pump 104 moves or expands the displaceable member 106 so as to push the liquid drug out of the reservoir 102. A cannula 108 connected to an outlet of the drug reservoir 102 conducts the liquid to an infusion set 109. The cannula 108 may be made of substantially impermeable tubing, such as medical-grade plastic. The infusion set 109 may include a catheter that is fluidically connected to the cannula 108 and delivers the drug to a subcutaneous tissue region. A lancet and associated insertion mechanism may be used to drive the catheter through the skin. Alternatively, the infusion set 109 may include another type of drug-delivery vehicle, e.g., a sponge or other means facilitating drug absorption through the skin surface.

The pump 104 may utilize any suitable pumping mechanism such as, for example, electrochemical, osmotic, electroosmotic, piezoelectric, thermopneumatic, electrostatic, pneumatic, electrohydrodynamic, magnetohydrodynamic, acoustic-streaming, ultrasonic, and/or electrically driven (e.g., motorized) mechanical actuation. In certain embodiments, electrolysis provides the mechanism that mechanically drives drug delivery. An electrolysis pump generally includes an electrolyte-containing chamber (hereinafter also referred to as the "pump chamber") and, disposed in the chamber, one or more pairs of electrodes that are driven by a direct-current power source to break the electrolyte into gaseous products. Suitable electrolytes include water and aqueous solutions of salts, acids, or alkali, as well as non-aqueous ionic solutions. The electrolysis of water is summarized in the following chemical reactions:

$$\text{anode:} \quad 2H_2O(l) \underset{\text{recombination}}{\overset{\text{electrolysis}}{\rightleftharpoons}} O_2(g) + 4H^+(aq) + 4e^-$$

$$\text{cathode:} \quad 2H_2O(l) + 2e^- \underset{\text{recombination}}{\overset{\text{electrolysis}}{\rightleftharpoons}} 2OH^-(aq) + H_2(g)$$

$$\text{Net:} \quad 2H_2O(l) \underset{\text{recombination}}{\overset{\text{electrolysis}}{\rightleftharpoons}} O_2(g) + 2H_2(g)$$

The net result of these reactions is the production of oxygen and hydrogen gas, which causes an overall volume expansion of the drug chamber contents. This gas evolution process proceeds even in a pressurized environment (reportedly at pressures of up to 200 MPa). As an alternative (or in addition) to water, ethanol may be used as an electrolyte, resulting in the evolution of carbon dioxide and hydrogen gas. Ethanol electrolysis is advantageous due to its greater efficiency and, consequently, lower power consumption, compared with water electrolysis. Electrolysis pumps in accordance with several embodiments are described in detail further below.

The pressure generated by the drug pump 104 may be regulated via a pump driver 110 by a system controller 112. For example, in an electrolytic pump, the controller 112 may set the drive current and thereby control the rate of electrolysis, which, in turn, determines the pressure. In particular, the amount of gas generated is proportional to the drive current integrated over time, and can be calculated using Faraday's law of electrolysis. For example, creating two hydrogen and one oxygen molecule from water requires four electrons; thus, the amount (measured in moles) of gas generated by electrolysis of water equals the total electrical charge (i.e., current times time), multiplied by a factor of ¾ (because three molecules are generated per four electrons), divided by Faraday's constant. The volume of the gas can be determined, using the ideal gas law, based on the pressure inside the pump chamber (and the temperature). Accordingly, by monitoring the pressure inside the pump chamber, it is possible to control the electrolysis current and duration so as to generate a desired volume of electrolysis gas, and thereby displace the same volume of liquid drug from the reservoir 102.

In certain low-cost embodiments, the dose of drug to be delivered from the reservoir 102 is dialed into the device using a mechanical switch (e.g., a rotary switch), which then activates the pump 104, via the controller 112, to deliver the dose. In various alternative embodiments, the controller 112 executes a drug-delivery protocol programmed into the device or commands wirelessly transmitted to the device, as further described below.

The system controller 112 may be responsive to one or more sensors that measure an operational parameter of the drug pump device 100, such as the pressure or flow rate in the drug reservoir 102 or cannula 108, the pressure inside the pump chamber, barometric pressure changes, or the position of the displaceable member 106. For example, the controller 112 may adjust the electrolysis based on the pressure inside the pump chamber, as described above; due to the inexpensiveness of pressure sensors, this option is particularly advantageous for pumps designed for quick drug delivery. Two or more pressure sensors may be placed in the pump chamber to simultaneously monitor pressure therein, which provides additional feedback to the controller 112, improves accuracy of information, and serves as a backup in case of malfunction of one of the sensors.

In pump devices that are intended to operate over multiple days, typically in accordance with a non-uniform delivery protocol (e.g., insulin delivery devices that are designed for 3-7 days of continuous drug delivery), a flow sensor is preferably used to measure drug flow out of the cannula in real-time, and compute the total dose delivered by integrating the flow rate over time. For safety, the device may include, in addition to the flow sensor, a pressure sensor inside the pump chamber. This ensures that, in case the flow sensor fails, the pressure sensor would be able to detect high drug delivery rates, and shut the pump down to avoid administering an overdose to the patient. It also provides extra safety by preventing chamber explosion at very high pressure when a failure mode occurs. Conversely, the combination of flow and pressure sensors can also detect a violation in the drug reservoir 102 if pressure is measured in the pump chamber but no flow is measured in the cannula 108, indicating a potential leak.

In general, the sensors used to measure various pump parameters may be flow, thermal, time of flight, pressure, or other sensors known in the art, and may be fabricated (at least in part) from parylene—a biocompatible, thin-film polymer. Multiple pressure sensors may be used to detect a difference in pressure and calculate the flow rate based on a known laminar relationship. In the illustrated embodiment, a flow sensor 114 (e.g., a MEMS sensor) is disposed in the cannula 108 to monitor drug flow to the infusion site, and detect potential obstructions in the flow path, variations in drug-pump pressure, etc. The cannula 108 may further include a check valve 116 that prevents backflow of liquid into the drug reservoir 112. Like the sensor 114, the check valve 116 may be made of parylene. In other embodiments, silicon or glass are used in part for the flow sensor 114 and valve 116 construction. The drug pump device 100 may include electronic circuitry 118 (which may, but need not, be integrated with the system controller 112) for processing the sensor signal(s) and, optionally, providing pump status information to a user by means of LEDs, other visual displays, vibrational signals, or audio signals. In addition to controlling the drug pump 104, the controller 112 may be used to control other components of the drug pump system; for example, it may trigger insertion of the lancet and catheter.

The system controller 112 may be a microcontroller, i.e., an integrated circuit including a processor core, memory (e.g., in the form of flash memory, read-only memory (ROM), and/or random-access memory (RAM)), and input/output ports. The memory may store firmware that directs operation of the drug pump device. In addition, the device may include read-write system memory 120. In certain alternative embodiments, the system controller 112 is a general-purpose microprocessor that communicates with the system memory 120. The system memory 120 (or memory that is part of a microcontroller) may store a drug-delivery protocol in the form of instructions executable by the controller 112, which may be loaded into the memory at the time of manufacturing, or at a later time by data transfer from a hard drive, flash drive, or other storage device, e.g., via a USB, Ethernet, or FIREWIRE port. In alternative embodiments, the system controller 112 comprises analog circuitry designed to perform the intended function, e.g., to deliver the entire bolus upon manual activation by the patient.

The drug-delivery protocol may specify drug delivery times, durations, rates, and dosages, which generally depend on the particular application. For example, some applications require continuous infusion while others require intermittent drug delivery to the subcutaneous layer. An insulin-delivery device may be programmed to provide a both a continuous, low basal rate of insulin as well as bolus injections at specified times during the day, typically following meals. To implement a dinner pump, for example, the instructions may cause the pump to administer a 150 μL dose of insulin immediately after dinner, and to dispense another 350 μL at a basal rate over eight hours while the patient sleeps. In general, drug pump devices 100 may be configured to achieve sustained drug release over periods ranging from several hours to several months, with dosage events occurring at specific times or time intervals. Flow rates of fluid flowing through the cannula 108 may range from nanoliters per minute to microliters per minute. A clinician may alter the pump programming in system memory 120 if the patient's condition changes.

Sensor feedback may be used in combination with a pre-programmed drug-delivery protocol to monitor drug delivery and compensate for external influences that may affect the infusion rate despite unchanged electrolysis (such as backpressure from the infusion site or cannula clogging). For example, signals from the flow sensor 114 may be integrated to determine when the proper dosage has been administered, at which time the system controller 112 terminates the operation of the pump 104 and, if appropriate, causes retraction of the delivery vehicle. The system controller 112 may also assess the flow through the cannula 108 as reported by the flow sensor 114, and take corrective action if the flow rate deviates sufficiently from a programmed or expected rate. If the system controller 112 determines that a higher flow rate of drug is needed, it may increase the current to the electrolysis electrodes to accelerate gas evolution in the electrolysis chamber; conversely, if the system controller 112 determines that a lower flow rate of drug is needed, it may decrease the current to the electrolysis electrodes.

The pump driver 110, system controller 112, and electronic circuitry 118 may be powered by a battery 122. Suitable batteries 122 include non-rechargeable lithium batteries approximating the size of batteries used in wristwatches, as well as rechargeable Li-ion, lithium polymer, thin-film (e.g., Li—PON), nickel-metal-hydride, and nickel cadmium batteries. Other devices for powering the drug pump device 100, such as a capacitor, solar cell or motion-generated energy systems, may be used either in place of the battery 122 or supplementing a smaller battery. This can be useful in cases where the patient needs to keep the drug-delivery device 100 on for several days or more.

In certain embodiments, the drug pump device 100 includes, as part of the electronic circuitry 118 or as a separate component, a signal receiver 124 (for uni-directional telemetry) or a transmitter/receiver 124 (for bi-directional telemetry) that allows the device to be controlled and/or re-programmed remotely by a wireless handheld device, such as a customized personal digital assistant (PDA) or a smartphone 150. A smartphone is a mobile phone with advanced computing ability that, generally, facilitates bi-directional communication and data transfer. Smartphones include, for example, iPhones™ (available from Apple Inc., Cupertino, Calif.), BlackBerries™ (available from RIM, Waterloo, Ontario, Canada), or any mobile phones equipped with the Android™ platform (available from Google Inc., Mountain View, Calif.).

The smartphone 150 may communicate with the drug pump device 100 using a connection already built into the phone, such as a Wi-Fi, Bluetooth, or near-field communication (NFC) connection. Alternatively, a smartphone dongle 152 may be used to customize the data-transfer protocol between the smartphone and the drug pump device 100, which facilitates optimizing the sender and/or receiver components 122 of the drug pump device 100, e.g., for reduced power consumption, and may provide a layer of security beyond that available through the smartphone. A smartphone dongle is a special hardware component, typically equipped with a microcontroller, designed to mate with a corresponding connector on the smartphone (e.g., a Mini USB connector or the proprietary iPhone connector). The connector may accommodate several power and signal lines (including, e.g., serial or parallel ports) to facilitate communication between the dongle and the smartphone and to power the dongle via the phone.

In certain embodiments, the smartphone 150 and pump device 100 communicate over a (uni- or bidirectional) infrared (IR) link, which may utilize one or more inexpensive IR light-emitting diodes and phototransistors as transmitters and receivers, respectively. Data transfer via the IR link may be based on a protocol with error detection or error correction on the receiving end. A suitable protocol is the IrDA standard for IR data communication, which is well-established and easy to implement. Communication between the drug pump device 100 and the smartphone 150 may also occur at radio frequencies (RF), using, e.g., a copper antenna as the transmitter/receiver component 124. The transmitter/receiver 124 and associated circuitry, which may collectively be referred to as the communication module of the drug pump device 100, may be powered by the battery 122 and/or by the signal transmitted from the smartphone 150 or other communication device. In some embodiments, the communication module remains in a dormant state until "woken up" by an external signal, thereby conserving power.

In some embodiments, the smartphone 150 is used to send real-time signals to the drug pump device 100, for example, to turn the pump on or off, or to adjust an otherwise constant drug delivery rate, and in some embodiments, the smartphone serves to program or re-program the drug pump device 100 for subsequent operation over a period of time in accordance with a drug-delivery protocol. The communication link between the smartphone and the drug pump device 100 may be unidirectional (typically allowing signals only to be sent from the phone and received by the drug pump device) or bi-directional (facilitating, e.g., transmission of status information from the drug pump device 100 to be sent to the smartphone). A special software application 154 (e.g., an iPhone "app") executing as a running process on the smartphone 150 may provide a user interface for controlling the drug pump device 100 via the smartphone display. As a security measure, the application 154 may be configured to be accessible only when the dongle 152 is connected to the smartphone 150. The application may further facilitate communication between the smartphone 150 and a remote party. For example, a health-care provider may communicate with his patient's smartphone 150 to obtain status updates from the drug pump device 100 and, based on this information, push a new drug-delivery protocol onto the patient's smartphone, which in turn uploads this new protocol to the drug pump device 100.

The functional components of drug pump devices as described above may be packaged and configured in various ways. In certain preferred embodiments, the drug pump device may be integrated into a patch adherable to the patient's skin. Suitable adhesive patches are generally fabricated from a flexible material that conforms to the contours of the patient's body and attaches via an adhesive on the backside surface that contacts a patient's skin. The adhesive may be any material suitable and safe for application to and removal from human skin. Many versions of such adhesives are known in the art, although utilizing an adhesive with gel-like properties may afford a patient particularly advantageous comfort and flexibility. The adhesive may be covered with a removable layer to preclude premature adhesion prior to the intended application. As with commonly available bandages, the removable layer preferably does not reduce the adhesion properties of the adhesive when removed. In some embodiments, the drug pump device is of a shape and size suitable for implantation. For example, certain pump devices in accordance herewith may be used to deliver drug to a patient's eye or middle ear. Ophthalmic pump devices may be shaped so as to conform to the patient's eyeball, and may include a suitable patch for adhesion to the eyeball.

The various components of the drug pump device may be held within a housing mounted on the skin patch. The device may either be fully self-contained, or, if implemented as discrete, intercommunicating modules, reside within a spatial envelope that is wholly within (i.e., which does not extend beyond in any direction) the perimeter of the patch. The housing may provide mechanical integrity and protection of the components of the drug pump device 100, and prevent disruption of the pump's operation from changes in the external environment (such as pressure changes). The control system components 110, 112, 118, 120, 122 may be mounted on a circuit board, which is desirably flexible and/or may be an integral part of the pump housing. In some embodiments, the electrodes are etched, printed, or otherwise deposited directly onto the circuit board for cost-savings and ease of manufacturing.

The housing may contain the infusion set 109. Alternatively, the infusion set 109 may be separately housed, mounted on a second skin-adhesive patch, and tethered to the drug pump device 100 via the cannula 108. Such a tethered infusion set 109 may be advantageous because it generally provides greater flexibility for the placement and orientation of the insertion set 109 and drug pump device 100 son the patient's skin. Further, it allows leaving the insertion set 109 in place while removing the pump device 100, for example, for the purpose of replacing or refilling the drug reservoir 102.

In some embodiments, the drug reservoir 102 and pump 104 are stacked in a double-chamber configuration, in which the drug reservoir 102 is separated from the pump chamber by a flexible diaphragm. Typically, the pump chamber is formed between the skin patch and the diaphragm, and the drug reservoir 102 is disposed above the pump 104 and formed between the diaphragm and a dome-shaped portion of the housing. In alternative embodiments, the drug pump device has a pen-injector configuration, i.e., the reservoir 102, a piston movable in the reservoir, and the pump 104 driving the piston are arranged in series in an elongated (e.g., substantially cylindrical) housing. A pump device with this configuration may be integrated horizontally into a skin patch for prolonged drug infusion. Alternatively, it may be used as a handheld injection device that is oriented substantially perpendicularly during injection, much like a conventional pen injector. Compared with the conventional injector that is mechanically activated by the patient, a digitally controlled electrolysis-based pump device as described herein provides the advantage of better dosage control. Various diaphragm pump and piston pump configurations are described in more detail below.

The drug-delivery device 100 may be manually activated, e.g., toggled on and off, by means of a switch integrated into the pump housing. In some embodiments, using the toggle switch or another mechanical release mechanism, the patient may cause a needle to pierce the enclosure of the drug reservoir 102 (e.g., the septum of a drug vial) to establish a fluidic connection between the reservoir 102 and the cannula 108; priming of the pump can then begin. Coupling insertion of the needle into the reservoir 102 with the activation of the pump device ensures the integrity of the reservoir 102, and thus protects the drug, up to the time when the drug is injected; this is particularly important for pre-filled drug pump devices. Similarly, the lancet and catheter may be inserted by manually releasing a mechanical insertion mechanism. In some embodiments, insertion of the lancet and catheter automatically triggers electronic activation of a pump, e.g., by closing an electronic circuit. Alternatively, the pump and/or insertion set may be activated remotely by wireless commands. Drug pump devices integrated into skin patches may also be configured to automatically turn on once the skin patch 102 is unwrapped and moisture is sensed. When drug delivery is complete, the device 100 may automatically retract the catheter and turn off the pump.

Drug pump devices 100 in accordance herewith may be designed for single or repeated use. Multi-use pumps generally include a one-way check valve and a flow sensor, as described above, in the cannula. Further, the drug reservoir of a multi-use pump may be refillable via a refill port, using, e.g., a standard syringe. In some embodiments, the drug pump device 100 is removed from the patient's skin for re-filling. The patient may, for example, place the drug pump device 100 and cartridge containing the new drug into a home refill system, where the pump device and cartridge may be aligned using, e.g., a press-machine mechanism. The patient may then press a button to trigger automatic insertion of a needle that draws liquid drug from the cartridge to the cannula in order to activate the electronics and begin priming the pump. In a further embodiment, a two-channel refill system may be used to aspirate old drug using one channel as well as load new drug into the drug pump device 100 using the other channel. One channel of the two-channel refill system is configured to regulate the flow and storage of drug, while the other one is configured to regulate the flow and storage of waste liquid. The system may use pneumatic pressure and/or vacuum control to direct the infusion and suction of liquid in and out of the drug pump, and may include sensors to monitor the pressures, and sterile filters to keep air from contaminating new drug. The drug pump device need not necessarily be removed from the patient for refilling with the two-channel system, as the system may provide sufficient and flow and pressure control to prevent accidental drug infusion into the target region (e.g., by infusing liquid below the cracking pressure of a check valve).

In some embodiments, multiple drug pump devices are integrated into one skin-adhesive patch. The devices may be arranged in an array on the same surface, stacked on top of one another, or a combination of both. They may share the same insertion set, or, alternatively, each device may have its own insertion set and drug outlet. A multiple-outlet arrangement facilitates administering several smaller doses over a larger surface area using multiple delivery vehicles, which may help to reduce systemic side effects (such as scarring and damage to subcutaneous tissue) that results from drug deliver at high concentrations to a small target area. In some embodiments, the multi-pump system includes, in addition to the drug reservoirs of the individual devices, a shared reservoir. During operation of any one of the pump devices, drug may be expelled from the respective reservoir into the shared reservoir, from where it is conducted to the infusion site.

The volume of drug stored in the various pump devices may be the same or varied, and may be as little as 50 μL or less. The pumps may function separately or collectively to deliver variable dosage volumes, essentially achieving controllable dosage resolution equal to an average dosage delivered by each pump. Parallel operation of the pumps may lead to faster response times and better control over the overall flow rate. For example, if a high flow rate is desired, all of the pumps may simultaneously be active. Further, the use of multiple, independently operable pumps provides redundancy, should any of the pumps fail.

In some embodiments, the individual drug reservoirs store different drugs, facilitating variable drug mixing through selective pump activation. Different drugs may be administered together as part of a drug "cocktail" or separately at different times, depending on the treatment regimen. Multiple reservoirs may also facilitate mixing of agents. For example, one reservoir may store, as a first agent, a drug that is in a "dormant" state with a half-life of several months, and another reservoir may contain, as a second agent, a catalyst required for activating the dormant drug. By controlling the amount of the second agent that reacts with the first agent, the drug delivery device is able to regulate the potency of the delivered dosage. The pumps may be operated by a single controller, which may be programmed to deliver the various drugs in accordance with a user-selected drug-delivery protocol. As explained above, pump operation may be altered through wireless reprogramming or control.

1. Piston Pump Devices

Figure 2:
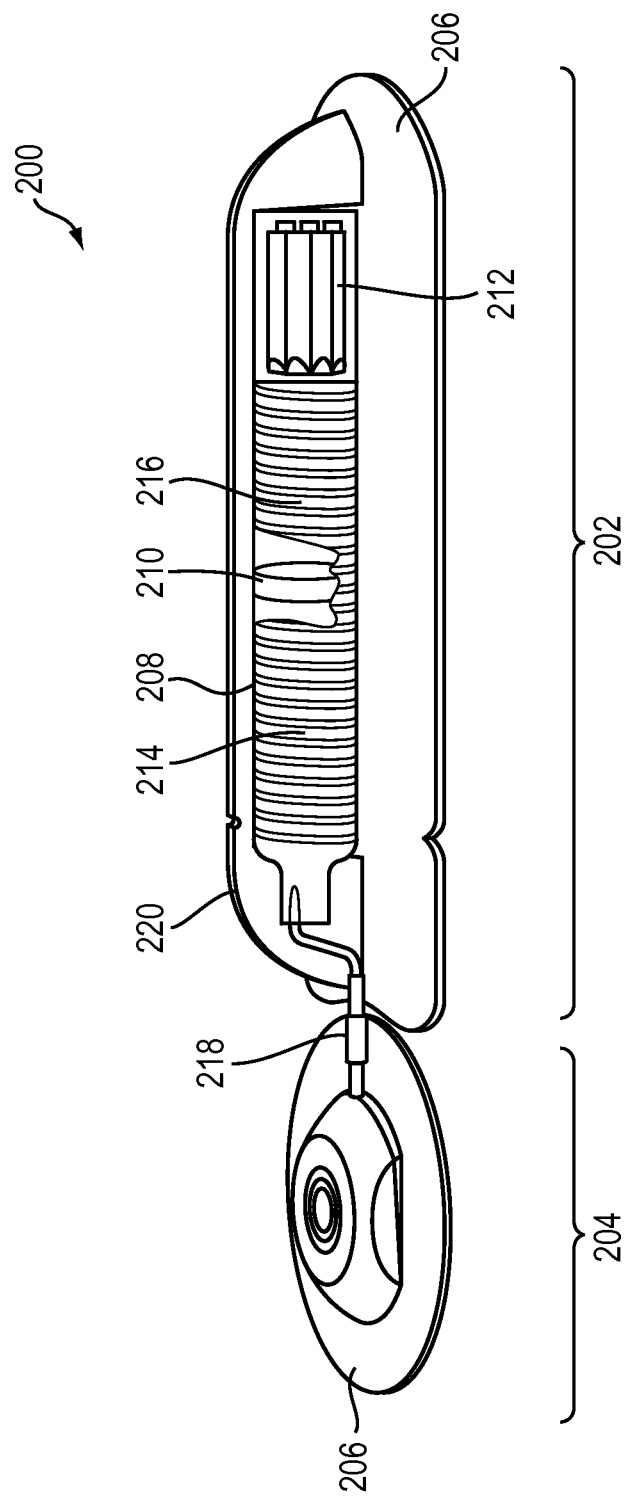
FIG. 2 is a perspective view of a piston pump device in accordance with one embodiment.

FIG. 2 shows an exemplary drug pump system 200 including a piston pump device 202 and an associated tethered infusion set 204, both mounted to skin-adhesive patches 206. The pump device 202 includes a cylindrical (or, more generally, tubular) vial 208 with a piston 210 movably positioned therein and an electrolysis electrode structure 212 mounted to one end. The structure 212 may be made of any suitable metal, such as, for example, platinum, titanium, gold, or copper. In another embodiment, the structure 212 may include a support made from plastic or glass containing the electrodes inside a sealed pump chamber. The piston 210, separates the interior of the vial 208 into a drug reservoir 214 and a pump chamber 216. A cannula 218 connects the drug reservoir 214 to the infusion set 204. The piston pump device 202 is enclosed in a protective housing 220, e.g., made of a hard plastic.

The vial 208 may be fabricated from a glass, polymer, or other materials that are inert with respect to the stability of the drug and, preferably, biocompatible. Glass is commonly used in commercially available and FDA-approved drug vials and containers from many different manufacturers. As a result, there are well-established and approved procedures for aseptically filling and storing drugs in glass containers, which may accelerate the approval process for drug pump devices that protect the drug in a glass container, and avoid the need to rebuild a costly aseptic filling manufacturing line. Using glass for the reservoir further allows the drug to be in contact with similar materials during shipping. Polymer vials, e.g., made of polypropylene or parylene, may be suitable for certain drugs that degrade faster when in contact with glass, such as protein drugs.

Suitable glass materials for the vial may be selected based on the chemical resistance and stability as well as the shatterproof properties of the material. For example, to reduce the risk of container breakage, type-II or type-III soda-lime glasses or type-I borosilicate materials may be used. To enhance chemical resistance and maintain the stability of enclosed drug preparations, the interior surface of the vial may have a specialized coatings. Examples of such coatings include chemically bonded, invisible, ultrathin layers of silicone dioxide or medical-grade silicone emulsions. In addition to protecting the chemical integrity of the enclosed drugs, coatings such as silicone emulsions may provide for easier withdrawal of medication by lowering internal resistance and reducing the amount of pressure needed to drive the piston forward and expel the drug.

In certain embodiments, the drug pump device is manufactured by fitting a conventional, commercially available glass or polymer drug vial, which may already be validated for aseptic filling, with the piston and electrolysis pump, as shown in FIG. 3A. The piston 300 may be disposed inside the vial 302 near one end, leaving room for the electrolysis pump 304, and a septum 306 may be disposed at the other end to seal the vial. Both the piston 300 and the septum 304 may be made of an elastomeric polymer material, such as a synthetic or natural rubber; in some embodiments, silicone rubber is used. A screw-in needle cassette 308 may be placed over the septum 304, as illustrated in FIG. 3B, and a mechanical actuation mechanism may serve to screw the cassette into the vial 302 such that the cassette needle punctures the septum 304 and establishes a connection with the cannula at the time the patient desires to use the pump. To accommodate the electrolysis pump 304, the vial 302 is, in some embodiments, longer than typical commercially available vials, but maintains all other properties such that validated filling methods and the parameters of existing aseptic filling lines need not be changed. The drug pump device may be furnished with a prefilled vial. If a glass vial is used, the drugs can be stored in the pump device for long-term shelf life without the need to change the labeling on the drug.

In applications involving dry-powder or lyophilized drug preparations, dual-compartment vials, also known as mix-o-vials, may be employed in the drug pump device. These vials may incorporate a top compartment containing a diluent solution and a bottom compartment containing a powdered or lyophilized drug. The two compartments may be separated by a rubber stopper. Electrolysis may be used to actuate a mixing system that triggers the piercing of the stopper to cause the top and bottom contents to mix before or during infusion. For lyophilized and powder medications, vials of borosilicate glass are particularly suitable. The vial bottom may be specially designed to optimize cake formation and enhance the efficiency of the reconstitution process. Borosilicate vials also offer good hydrolytic resistance and small pH shifting, and are not prone to delamination. They are commercially available in both clear and amber varieties, with capacities ranging currently from 1.5 to 150 $cm^3$.

Figure 4A:
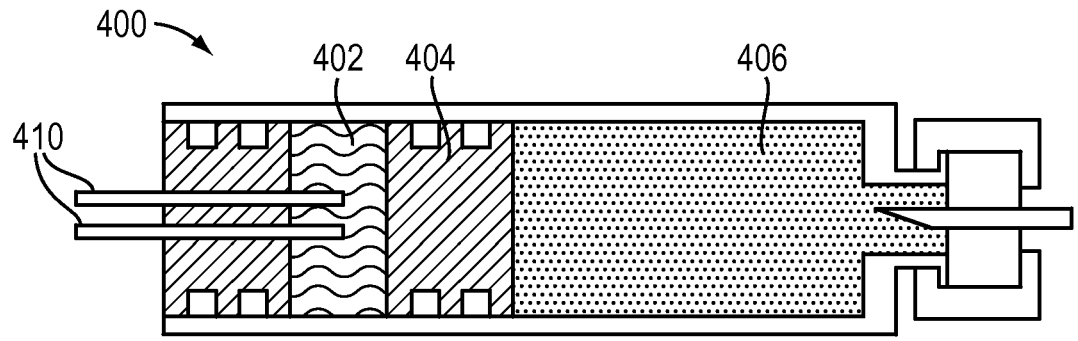
FIGS. 4A-4C are drawings of a piston pump device with a liquid-electrolyte-based electrolysis pump at various stages during drug delivery, illustrating the location of an electrode pair relative to the electrolyte level in the electrolysis chamber.
Figure 4B:
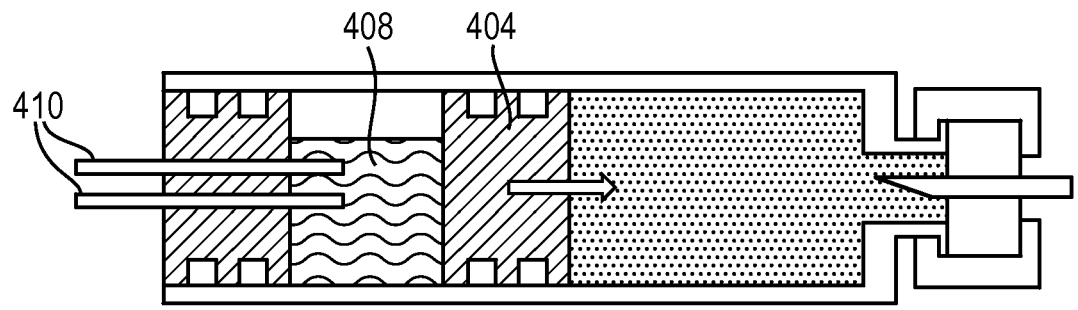
Figure 4C:
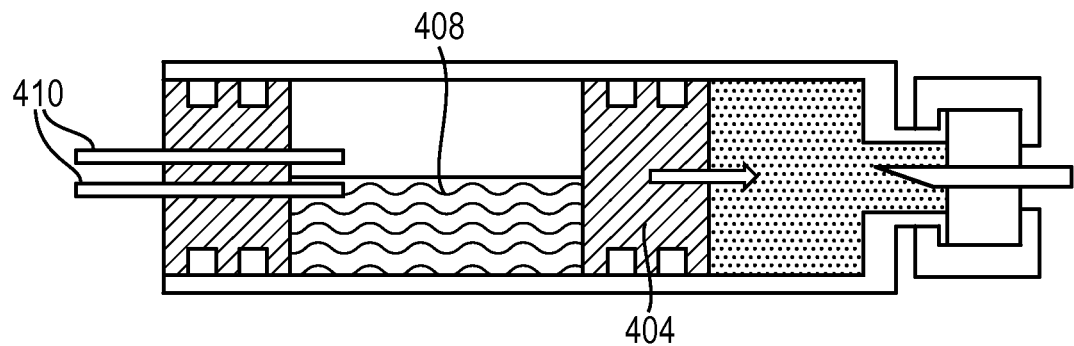

FIG. 4A illustrates schematically a piston pump device 400 having a conventional electrolysis pump chamber 402 filled with liquid electrolyte. As gaseous electrolysis products are generated, they push the piston 404 towards the outlet end of the drug reservoir 406 (see FIG. 4B). Movement of the piston 404 increases the volume of the electrolysis chamber 402, causing a decrease in the level of the electrolyte 408. Depending on the orientation of the device, one or both electrodes 410 may, as a result, gradually emerge from the electrolyte and become surrounded by the gas, eventually forming an open circuit (FIG. 4C). This causes the electrolysis reaction to cease. Various drug pump embodiments that avoid this problem are described below.

Figure 5A:
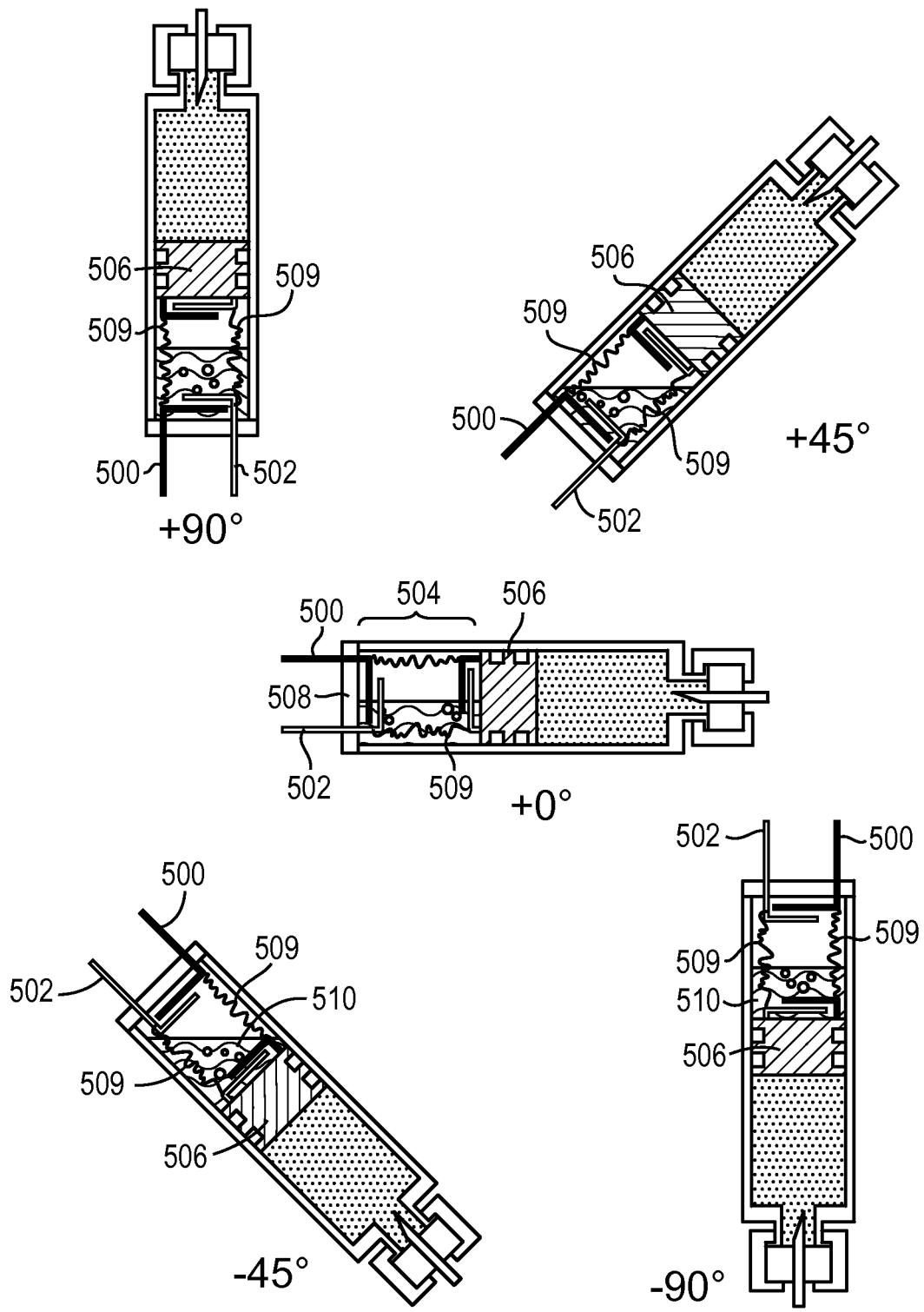
FIGS. 5A-5F are drawings of piston pump devices with liquid-electrolyte-based electrolysis pumps in accordance with various embodiments, illustrating various electrode arrangements that ensure contact of the electrodes with the electrolyte regardless of the orientation of the devices.
Figure 5B:
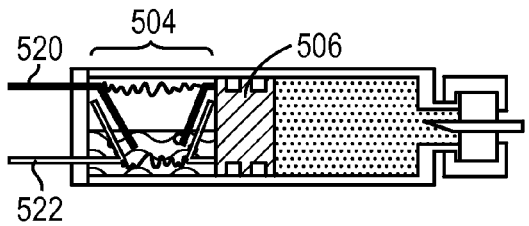

In some embodiments, the electrodes are arranged such that at least a portion of each electrode remains submerged in electrolyte partially filling the electrolysis chamber regardless of the device orientation. For example, as illustrated in FIG. 5A, electrode pairs 500, 502 may be located on both ends of the electrolysis chamber 504, i.e., at or near the interface of the electrolysis chamber 504 with the piston 506 as well as at the opposite wall 508 sealing the vial. The cathodes 500 and anodes 502 on either side of the electrolysis chamber 504 may be connected by a flexible wire 506 of sufficient length to accommodate separation of the two walls of the electrolysis chamber 504 as electrolysis proceeds and the contents of the vial are expelled. As illustrated by the five depicted device orientations at 0°, ±45°, and ±90° with respect to a horizontal plane, this electrode arrangement ensures at least partial submergence of the electrodes 500, 502 in the electrolyte 510 regardless of orientation. Changes in orientation as depicted arise, as a practical matter, from different patient orientations during sleep or activity, throughout which drug delivery needs to continue. FIG. 5B shows a modification of this electrode arrangement, in which the electrode pairs 520, 522 are angled relative to the walls of the electrolysis chamber 504. In the example shown in FIG. 5C, multiple electrode pairs 530, 532 are positioned on each side of the electrolysis chamber 504.

Figure 5D:
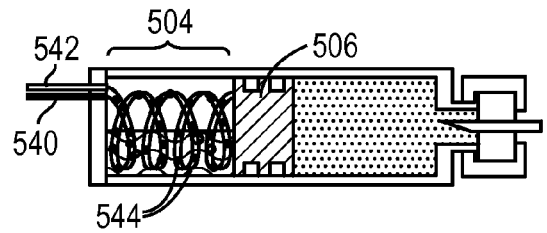
Figure 5C:
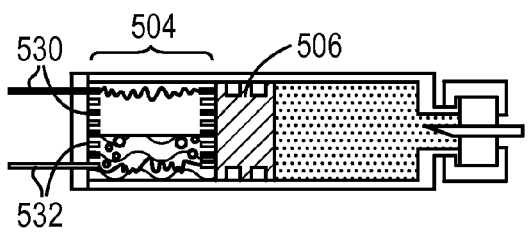
Figure 5E:
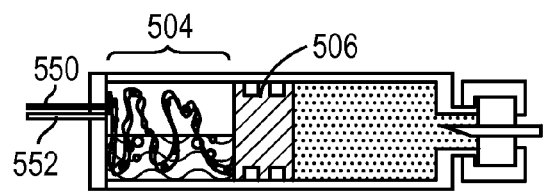

FIG. 5D shows an embodiment in which two parallel electrode spring coils 540, 542 are utilized. These two coils 540, 542 may be supported by a series of electrically isolating spacers 544 in a ladder-like configuration that prevents short circuits between the two coils 540, 542. This double coil set is compressed into the electrolysis chamber 504 so that, as the piston moves forward, the coils extend to keep part of the coil pair submerged in electrolyte 510. This arrangement may be modified by disposing multiple coil pairs 540, 542 in the electrolysis chamber 504 to provide redundancy in case of a short circuit between the coils of any coil pair. In yet another embodiment, illustrated in FIG. 5E, a flexible parallel pair of wires 550, 552 separated by multiple spacers 544 in a ladder-like configuration is utilized. One end of this wire pair 550, 552 is affixed to the piston 506, and the other end is attached to the opposing wall of the electrolysis chamber 504. As the piston 506 moves, at least part of the wire pair 550, 552 will remain submerged in electrolyte for continuous and steady gas generation.

Figure 5F:
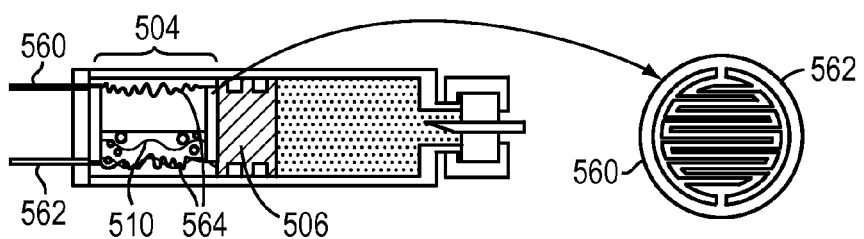

In another embodiment, illustrated in FIG. 5F, two pairs of interdigitated microelectrodes 560, 562 are used, one attached to the piston 506 and the other one located at the opposite, fixed wall of the electrolysis chamber 504. The cathodes 560 of the microelectrode sets on both ends of the electrolysis chamber 504 may be connected with a flexible wire 564, as may the two opposed anodes 562. In this arrangement, as in the previous examples, part of the electrode pair 560, 562 will be submerged in electrolyte 510 to continuously produce electrolysis gases irrespective of the orientation of the pump device. As will be evident to those skilled in the art, other electrode designs may also be used to ensure immersion of at least a portion of an electrode pair in the electrolyte.

Figure 6:
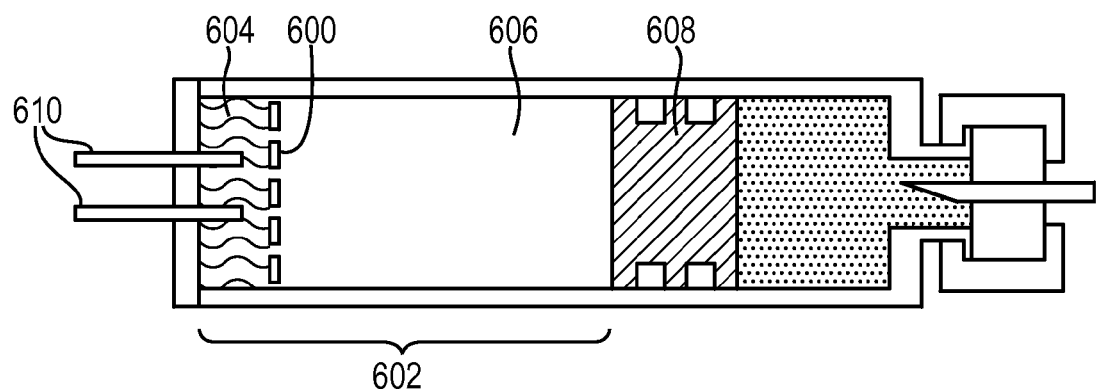
FIG. 6 is a schematic drawing of a piston pump device including a gas-permeable separator in the electrolysis chamber in accordance with one embodiment.

In some embodiments, schematically illustrated in FIG. 6, a gas-permeable separator 600 partitions the pump chamber 602 into an electrolyte-filled compartment 604 at the back end and a gas compartment 606 adjacent the piston 608. The gas-permeable separator 600 is generally impermeable to liquid electrolyte, but allows gaseous electrolysis products to pass. Suitable separators are known to persons of skill in the art, and include, for example, thin silicone membranes, polymer membranes (e.g., made of polyurethane, carboxylated poly(vinyl chloride), or parylene), microporous polymer films with polymeric coatings, or porous metal films. The separator 600 is fixedly mounted within the pump chamber 602; as a result, the electrolyte compartment 604 has a constant volume. As an electrode pair 610 disposed in the electrolyte compartment 604 breaks down liquid electrolyte into gas products, the gas penetrates the separator 600, entering the gas compartment 606 and driving the piston 608 forward; consequently, the volume of the gas compartment 606 increases. Due to the large expansion ratio associated with the phase transition from liquid electrolyte to gaseous products, the volume of the gas compartment 606 generally increases orders of magnitude (e.g., hundreds- or thousandfold) faster than the volume of liquid electrolyte in the electrolyte compartment 604 decreases. As a result, the electrodes 610 remain submerged in the electrolyte throughout significant displacement distances of the piston 608. The volume of the electrolyte compartment may be chosen, based on the expansion ratio of the employed electrolyte and the initial drug reservoir volume, such that contact between the electrodes and the electrolyte is ensured until the drug has been fully expelled.

Yet another approach involves absorbing the electrolyte within a matrix that fills the interior of the pump chamber, or at least a portion of the chamber containing the electrodes. The matrix may be any absorbent, three-dimensionally networked material, for example, the solid phase of a gel, cotton, a superabsorbent polymer, a sponge material, or any combination thereof (such as, e.g., a gel absorbed within a sponge). Its function is to maintain a persistent distribution of the electrolyte throughout the matrix, thereby ensuring that the electrodes, which are embedded in or filled with the matrix, remain in contact with electrolyte.

Additional examples of suitable matrix materials include other fibers such as natural or synthetic cellulose based materials (e.g., rayon), acetate fiber, nylon fiber, hemp, bamboo fabric, wool, carbon based fibrous material, silk, polyester, or other cotton-blend fibers. Ultra-fine cellulose nanofibers (with diameters of 1-50 nm), made using, for example, a combination of TEMPO, NaBr, and/or NaCIO oxidation of natural cellulose (e.g., wood pulp), in different nanofibrous composite formats include small diameter, high surface-to-volume ratio, easy surface functionality, good mechanical properties, and good chemical resistance. Fibers with hydrophilic and water-absorbent properties tend to be preferable; they include "polymer molecules" that are linked up in repetitive patterns or chains, negative charged materials that help attract and absorb "dipolar" water molecules, and fibers with capillary action, where the fibers are able to draw or suck in water like a straw through the interior of the fiber. Capillary action is present both in the fiber of the cotton plant and cotton fabric. Once drawn in through the fibers, the water is then stored in the interior cell walls.

A particularly advantageous matrix material is hydrogel, a highly water-absorbent network of hydrophilic polymer chains. Hydrogels can contain large fractions (e.g., more than 99% by weight) of water or an aqueous solution. They are highly biocompatible, and their absorbed liquid maintains most of its original liquid properties (e.g., density, phase change, and incompressibility), which makes the gels stable for mechanical operation. Using hydrogel also facilitates easier packaging in low-cost manufacturing.

Electrolytes used with the hydrogel system may generally be aqueous solutions, i.e., solutes dissolved in water. Examples of solutes include salts (e.g., sodium chloride, magnesium sulfate, or sodium sulphate), dilute acids (e.g., sulfuric acid, hydrochloric acid, or amino acid), and dilute alkali (e.g., sodium hydroxide, potassium hydroxide, calcium hydroxide). Instead of water, other liquids, such as oil or ethanol, may be used as solvents. Depending on the electrolyte used, the electrolysis gas includes a combination of hydrogen, oxygen, and/or carbon dioxide. For example, electrolysis of water results in oxygen and hydrogen gas, whereas electrolysis of ethanol results in carbon dioxide and hydrogen gas. The use of ethanol may lower the power consumption of the electrolysis pump and extend the life of the battery.

In some embodiments, the water contained in the hydrogel itself serves as the electrolyte. The volume expansion from liquid water to hydrogen and oxygen gas is more than a thousand times. Consequently, a pump chamber volume of less than $1/1000$ that of the drug reservoir may, at least theoretically, suffice to expel all the drug from the reservoir. However, to increase the reliability of the electrolysis pump, a volume ratio such as 1 to 5 (electrolysis chamber to drug reservoir) may be preferable. For example, for drug reservoir volumes of 0.5 mL, 3 mL, or 5 mL, the corresponding volume of electrolysis chamber may be 0.1 mL, 0.6 mL, or 1 mL, respectively. Still, use of an electrolysis pump permits the size of the pump to be reduced significantly compared with conventional drug pumps, such as, e.g., motorized drug pump devices.

The matrix material may be placed next to electrodes in a single pump chamber, or in multiple electrolysis cells (e.g., as described with respect to FIGS. 7A-7D below). FIG. 3A shows a basic single-chamber configuration of a gel-based electrolysis pump, in which a pair of electrode poles breaks the electrolyte contained in the gel into gas bubbles (e.g., hydrogen bubbles and oxygen bubbles), which cause expansion of the bubble-gel mixture. The expanding gel mechanically couples the pump chamber to the piston. In place of electrode poles, more complex electrode structures, such as planar interdigitated electrodes (as shown in FIG. 11B in the context of a diaphragm pump device) may be used. In an alternative embodiment, a coaxial electrode pair having a pole-shaped core electrode arranged along the axis of a tubular (e.g., cylindrical) sleeve electrode may be used.

In some embodiments, multiple coaxial electrode pairs, which are preferably arranged in parallel in a close-packed pattern, are used to compartmentalize the pump chamber into several electrolytic cells. The individual cells may be driven separately or in combination, which facilitates precise and smooth actuation of the piston. Operating the cells consecutively may contribute to maintaining contact between the hydrogel and the respective active electrode pair while gas is generated over time. A multi-cell electrode structure also increases the reliability of the pump device due to redundancy: because of the large volume expansion ratio, a single cell may be able to drive the piston from the beginning to the end of drug delivery. In some embodiments, the electrolysis cells are activated in a serial fashion, one after the other as electrolyte in the respective active cells dries out, to prolong the overall lifetime of the pump; cell activation may be controlled by the electronic circuitry and based, for example, on a measured electrolysis or flow rate.

Figure 7C:
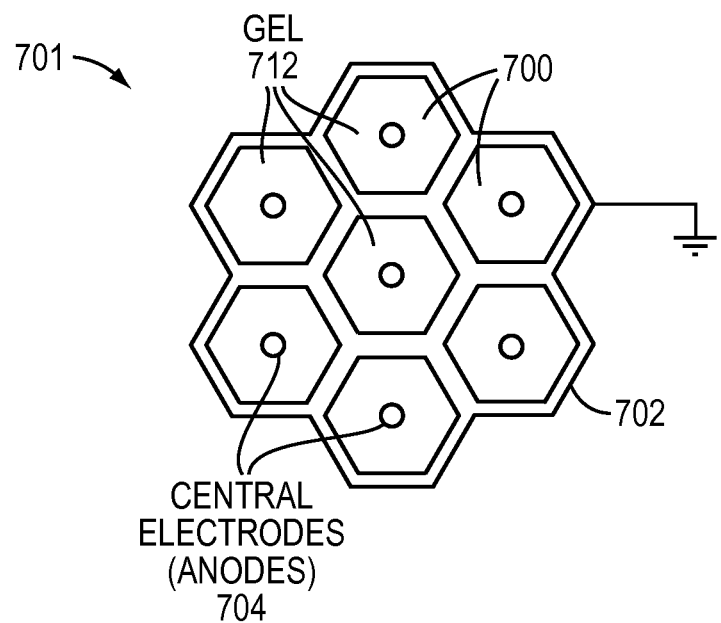
FIG. 7C shows the honeycomb electrode structure of FIGS. 7A and 7B in cross section.

FIGS. 7A and 7B illustrate drug pump embodiments that include multiple electrolytic cells 700. Here, seven co-axial electrode pairs with hexagonal cross sections are arranged in a honeycomb structure 701, which is shown in front-view in FIG. 7C. The tubular sleeve electrodes may (but need not) form a contiguous hexagonal latticework 702, and may be manufactured from off-the-shelf metallic micro-honeycomb tubes. Typically (although not necessarily), the core electrodes 704 serve as the anodes and the latticework 702 serves as the cathodes of the respective cells.

At the beginning of drug delivery from a filled reservoir 706, the honeycomb electrode structure may extend through the drug pump chamber, from the back wall 708 of the chamber to the piston 710, as illustrated in FIG. 7B. As electrolysis gases are generated, the drug chamber expands and the piston 710 moves towards the drug outlet. In some embodiments, the expanding gel 712 flows out of the tubular electrolysis cells 700 and enters the space between the cells 700 and the piston 710. In the alternative embodiment shown in FIG. 7D, the electrode cells 700 are sealed by a porous membrane or other gas-permeable filter 714, which may be, as described above, a thin silicone membrane, a polymer membrane or a microporous polymer film. The filter 714 serves to retain the gel 712 and electrolyte inside the electrolysis cells 700 while allowing gas to leave the cells 700 and fill and expand the space between the cells and the piston 710.

Figure 7D:
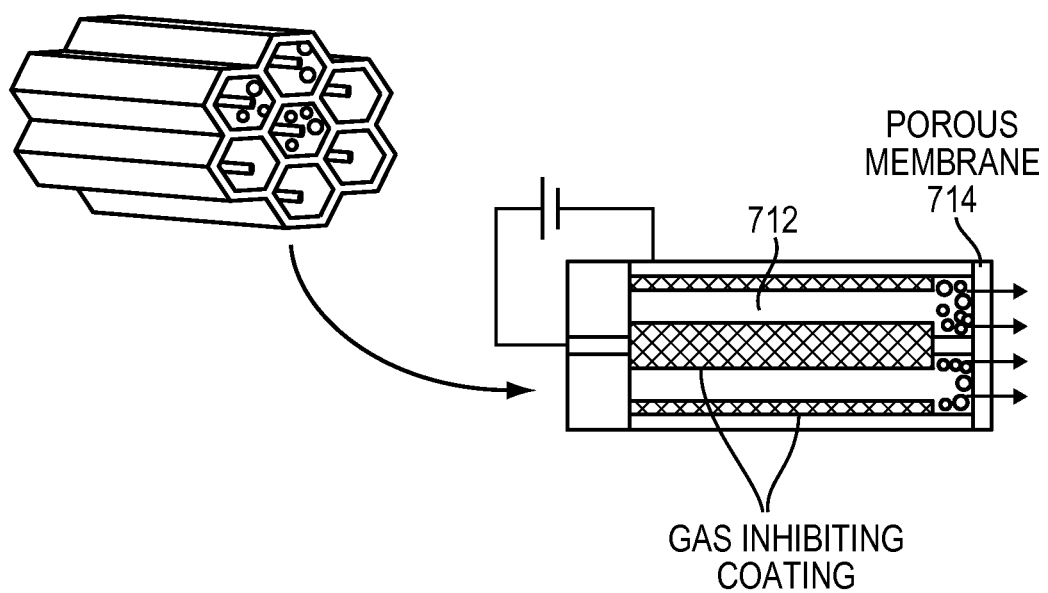
FIG. 7D shows a membrane-sealed honeycomb electrode structure with a gas-inhibiting surface coating in accordance with one embodiment.

In some embodiments, large portions of the interior surfaces of the honeycomb electrodes 702 and portions of the core electrodes 704 are coated with a material that inhibits gas formation, such as epoxy, while surface portions of the electrodes near the gas-permeable filter 714 are exposed (see FIG. 7D). For example, 10% or less of the electrode surface area may be uncoated. As a result of the coated and uncoated areas, gas will be generated proximally to the filter 714, allowing hydrogel (and/or electrolyte) to be preserved inside the electrolytic cells 700 for longer periods.

Some electrolysis pumps, such as smaller implantable pumps for drug delivery to the eye or the middle ear, or refillable drug pumps (where a diaphragm or piston collapses back to its initial state after the drug has been refilled) desirably use a non-expanding fibrous material for the matrix. Otherwise, expansion of the matrix could limit the collapse of the piston or diaphragm, and prevent the drug reservoir from being fully refilled A non-expanding fibrous material can keep electrolyte near the electrodes, but does not interfere with the piston or diaphragm motion.

Electrolysis pumps as described above generally facilitate continuous control of the drug-delivery rate via the drive voltage or current applied to the electrodes. However, as the piston moves inside the drug vial, sudden changes in friction between the piston and the vial may cause the drug delivery rate to deviate from the intended delivery protocol, resulting, for example, in a non-uniform delivery rate despite a constant rate of electrolysis, or in undesired spikes in an otherwise smooth uniform or non-uniform delivery protocol. Such changes in friction typically occur at the onset of piston movement as a consequence of the difference between static and dynamic coefficients of friction: the static coefficient of friction between the piston and vial generally exceeds the dynamic coefficient of friction (usually by a factor of about two or three), so that the force needed to start the piston in motion is greater than that needed to keep it moving. In addition, if the piston stops moving for a short period of time, a larger force is needed to re-initiate piston movement.

Furthermore, the dynamic friction itself may be affected by variations in the surface properties of the piston and/or the vial along their lengths, and/or by changes in the surface properties resulting from the interaction between piston and vial. For example, if the inner diameter of the vial and/or the outer diameter of the piston vary slightly along their lengths, the frictional forces generally depend on the piston position. Further, surface roughness may be smoothened out in time, in particular, if a refillable drug pump device is used repeatedly. Conversely, discrete surface defects, e.g., a peck sticking out from the interior surface of a glass vial, may roughen and/or damage the other surface, e.g., the surface of a soft rubber piston. In general, the variations in dynamic friction due to these and other effect are highly unpredictable.

Figure 8:
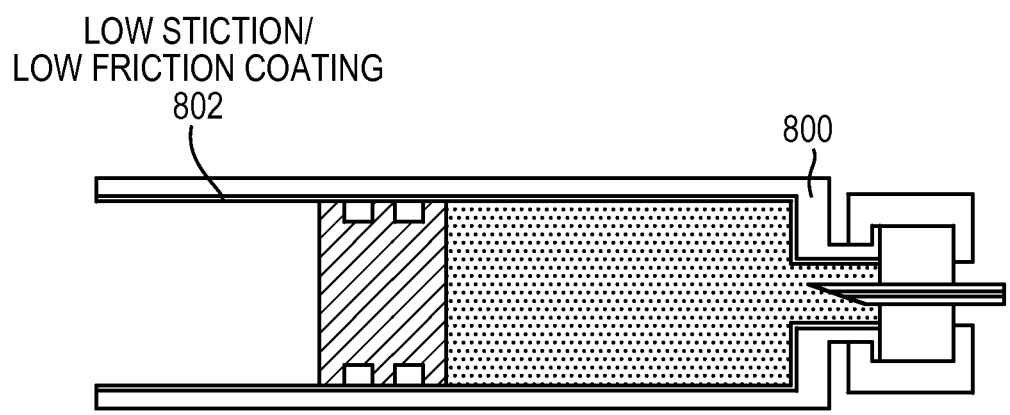
FIG. 8 is a schematic drawing of a piston pump vial with an interior surface coating in accordance with one embodiment.

The difference between static and dynamic friction may be reduced by applying a suitable surface coating to the interior surface of the vial and/or to the piston. In some embodiments, the vial (which may be made, e.g., of glass) is coated with a low-friction material such as, for example, parylene or polytetrafluoroethylene (commonly known under the brand name Teflon™), which reduces static friction without significantly changing dynamic friction. Because vial surface coatings may be in contact with drugs or drug solutions, the coating materials are preferably biocompatible to facilitate long-term drug stability. FIG. 8 illustrates a drug vial 800 with an interior surface coating 802.

While the friction drop at the onset of piston movement can be mitigated with friction-reducing coatings, and variations in dynamic friction can be minimized through high-precision manufacturing and selection of suitable combinations of piston and vial materials, in general they cannot be eliminated entirely. This problem may be addressed by using pressure variations in the drug chamber to match the applied force to the friction profile in order to maintain a desired piston velocity (or to change the piston velocity according to a desired protocol). For this purpose, some drug pump embodiments include one or more sensors to continuously monitor a parameter indicative of or affecting drug delivery. For example, a flow or pressure sensor placed inside the cannula may be used to measure the drug delivery rate directly, and feedback circuitry can be employed to adjust the rate of electrolysis in response to sensed variations that deviate from the delivery protocol.

Alternatively, the movement of the piston may be monitored with a position or velocity sensor. For example, in one embodiment, illustrated in FIG. 9, a magnet 900 is embedded in the piston 902, and an induction coil or coil sleeve 904 is wound around the drug vial such that, as the magnet 900 moves relative to the coil 904, an electric voltage proportional to the piston velocity is induced in the coil 904. To ease manufacturing, the piston 902 may be molded or otherwise manufactured to accommodate the magnet 900 in a small pocket, allowing the magnet to be press-fit into place in a simple assembly step. A lip may be included to hold the magnet in place. In yet another embodiment, the pressure inside the pump chamber is measured continuously, allowing a sudden friction decrease or increase to be detected via a pressure drop or spike, respectively.

In response to the measured flow, pressure, position, or other parameter, the system controller 112 may adjust the electrolysis rate in real-time (or near real-time, e.g., within 1 ms of the friction change) to compensate for any variations in friction. Alternatively or additionally, for changes in friction that are relatively predictable (such as the drop in friction at the onset of piston motion), the necessary adjustments to the electrolysis may be determined empirically. For example, to avoid flow rate spikes as the piston begins to move, the transition from static to dynamic friction may be repeated multiple times while the electrolysis rate and piston position and/or flow rate in the cannula are measured simultaneously. From this data, the electrolysis rate, as a function time, that is required to assure a smooth onset of piston motion may be calculated, and then programmed into the pump device. The friction compensation techniques and features described above apply similarly to a piston pump device that employs a pump mechanism other than electrolysis, i.e., the pump rate may, generally, be controlled based on a measured drug delivery parameter to reduce or eliminate the effect of changes in friction on the drug delivery rate.

Figure 9:
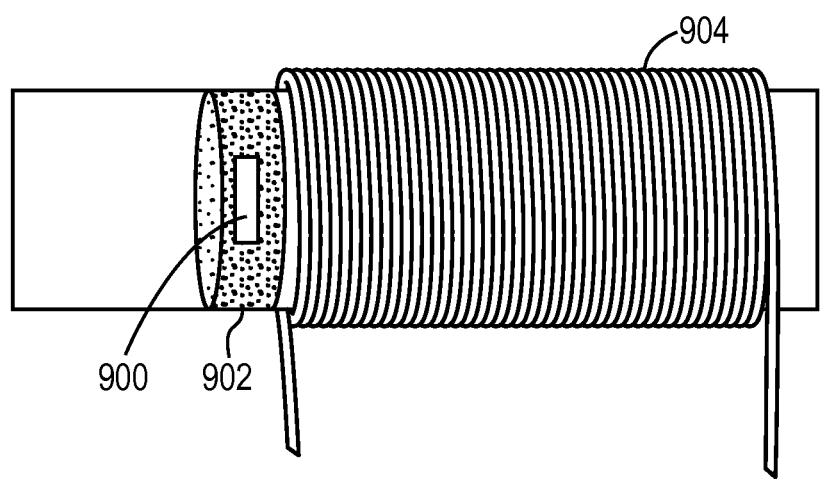
FIG. 9 is a schematic drawing of a magnetic-induction-based piston velocity sensor in accordance with one embodiment.

When operating a drug pump device to inject liquid drug into a patient, it is often desirable to monitor the rate or volume of the injection or to track the filling status of the device, e.g., to alert the patient of the need to refill the device soon. This can be accomplished by monitoring the position of the piston inside the vial. One approach utilizes the magnet 900 and one or more induction coils 904, as shown in FIG. 9. As the voltage induced due to the motion of the magnet 900 relative to the coil 904 is proportional to the momentary velocity of the piston 902, integration of the voltage over time yields the piston position. Integrator circuits are well known in the art and can be implemented without undue experimentation. This embodiment can be useful when a simple, inexpensive pump is needed.

Rather than continuously monitoring the position of the piston, it often suffices to detect and signal certain threshold piston positions corresponding to incremental amounts of drug remaining inside the vial, as depicted in FIGS. 10A-E. For example, an electronic display may indicate when the drug reservoir is completely filled (corresponding to a piston position at the farthest possible distance from the drug outlet to the cannula), 75% filled, 25% filled, or empty.

Figure 10A:
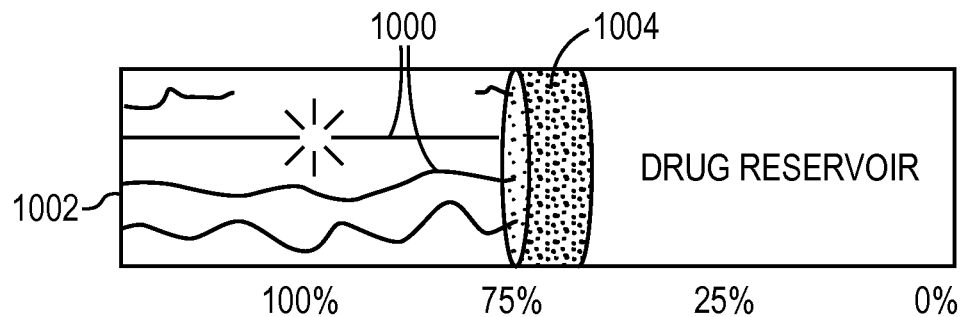
FIGS. 10A-10E are schematic drawings of piston position sensors in accordance with various embodiments.

For example, FIG. 10A shows a low-cost embodiment in which the piston position is mechanically sensed with strings of different lengths. The strings 1000 may be tethered from the back wall or electronics end 1002 of the drug pump chamber to the piston 1004. As the piston 1004 moves to push liquid out of the drug reservoir, the strings 1000 are stretched until they break. Based on the ultimate tensile strengths of the string material, the lengths of the strings are chosen such that each string ruptures when the piston 1004 reaches a corresponding predetermined position. For example, the string that is intended to break when the drug device is 75% filled has a length, immediately prior to breakage, that is the sum of the length of the drug chamber and a quarter of the maximum length of the drug reservoir. The strings 1000 may be, for example, nylon strings or fine metal (e.g., copper or lead) wires. If the vial and drug pump housing are transparent, string rupture may be observed by eye. Alternatively, if the strings are electrically conductive (as is the case with metal wires), their breakage may be detected electronically. For example, the several wires of different lengths may be part of respective electronic circuits, and their rupture may cause a detectable open-circuit condition.

Figure 10B:
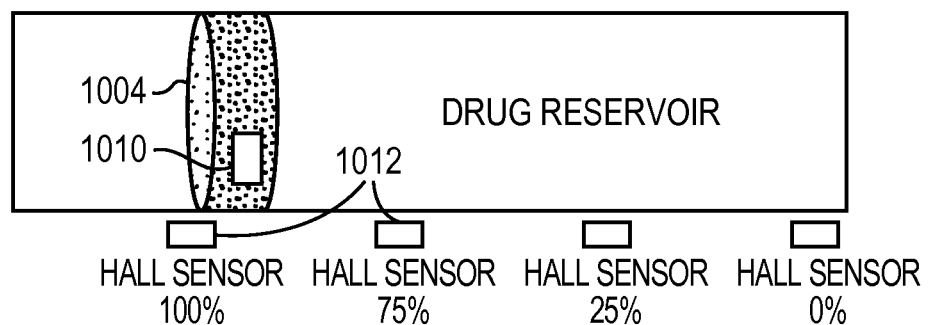
Figure 10C:
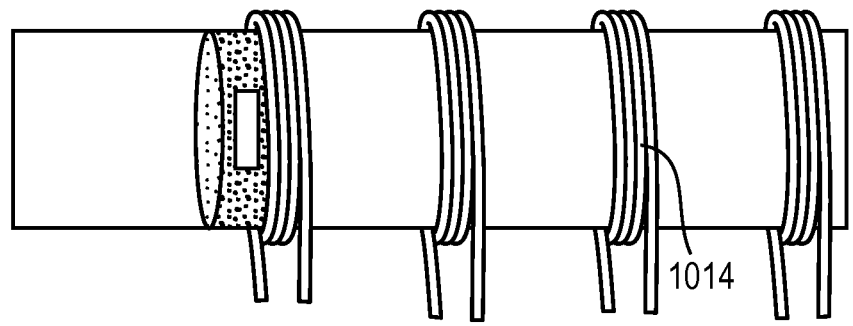
Figure 10D:
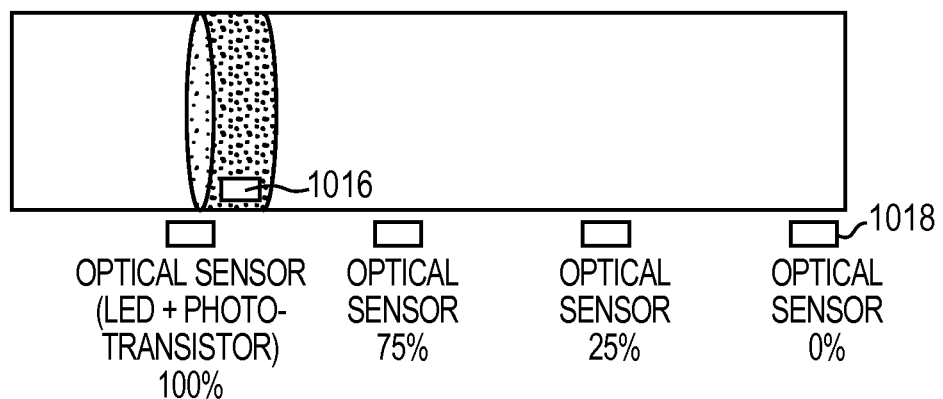
Figure 10E:
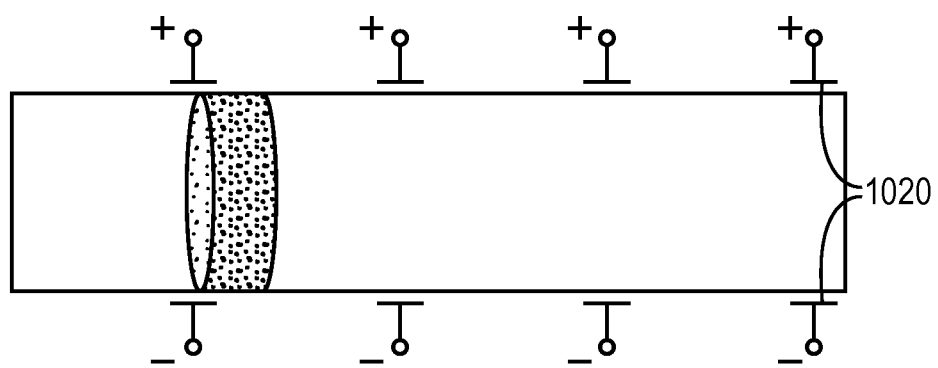

Position sensing may also be accomplished using multiple Hall effect sensors, optical sensors, induction coils, and/or capacitive sensors placed at different locations along the drug vial in combination with a magnet or optical component embedded in or attached to the piston; several embodiments are illustrated in FIGS. 10B-10D. For example, when a magnet 1010 associated with the piston 1004 passes a Hall effect sensor 1012 (FIG. 10B), the magnetic field strength detected by the sensor peaks, resulting in a voltage signal at that sensor. Similarly, as the magnet 1010 passes an induction coil 1014 (FIG. 10C), a voltage signal is detected, enabling precise location of the piston. To detect the piston motion optically, an LED may be attached to the piston and phototransistors may be placed alongside the vial to detect LED light as the piston passes. Alternatively, as shown in FIG. 10D, the piston may include a reflector 1016 (e.g., a piece of metal), and pairs of LEDs and phototransistor 1018 positioned along the vial may serve, respectively, to emit light and to measure the amount of reflected light, which reaches a maximum when the reflector 1016 is closest to the phototransistor.

To detect the piston motion using capacitive sensing, one or multiple pairs of plate-electrodes 1020 are positioned along the length of the vial such that the piston 1004 moves between consecutive pairs of plate-electrodes as the drug is dispensed. As the piston moves between a pair of plate-electrodes, the dielectric medium between those particular plate-electrodes changes, thereby producing a detectable change in capacitance between the two plate-electrodes 1020. The piston 1004 may be made from or contain material(s) that maximize the detectable change in capacitance, e.g., the piston may possess significantly different dielectric properties than the drug in the vial.

Piston drug pump devices as described above may be manufactured from various readily available components, and prefilled using existing fill/finish lines with few modifications. For example, as explained above, a conventional, FDA-approved drug glass vial may be used to house the drug reservoir. A rubber stopper, optionally having a magnet attached thereto, may be placed into the vial to serve as the piston. The electrolysis chamber may be housed in a container that is open on one side so as to allow mechanical coupling between its contents and the piston. A circuit board including the pump driver, system controller, memory, any other electronic circuitry, and battery (or other power supply) may be attached to the back-end of the electrolysis chamber, which may be made of ceramics or plastics and include electrical feedthroughs that allow electrical connections between the electrodes and the circuit board components. The circuit board may have the same or a similar diameter as the drug vial and pump, and may form, or be integrated into, a cap that fits onto the pump. Alternatively, if the circuit board is larger than the pump diameter, it may be placed to the side of the drug vial and pump assembly. The chamber may be filled with electrolyte-absorbed hydrogel, and then fitted into (or onto) the back-end of the vial, thereby closing the vial.

The pump container may be made of glass. Its back-end may be sealed by heating it, e.g., in an oven or with a torch, and then crimping, twisting, or otherwise closing it, by hand or with a specially designed jig, while the glass is molten. The electrolysis electrodes may be positioned and sealed in place as the glass is crimped. In some embodiments, the glass container holding the pump may be placed over a portion of the open drug vial like an end-cap. In other embodiments, the glass container is slid partially into the vial. Either way, the overlapping wall portions of the vial and pump container may be bonded with an adhesive sealant or through application of heat. In embodiments that utilize a honeycomb electrode or similar structure, this structure may, itself, serve to contain the other drug pump components (such as the hydrogel or other matrix material), and may be placed into the glass vial and secured, e.g., by a clamp-fit or screw mechanism. To prevent leakage of the electrolyte out of the electrolyte chamber (which could cause a short circuit in the circuit board), the electrolysis chamber may be sealed with a rubber O-ring.

Once the vial, piston, and pump are assembled, they may be sterilized, for example, by gamma-irradiation. One of the advantages of hydrogel and electrolysis fluid is that they can readily be gamma-irradiated after assembly. Sterilization serves to protect the patient from infection by preventing bacteria and pyrogens from entering the final fluid pathway of the device. The drug vial may initially be sterilized through standard techniques, for example, the use of heat or radiation. In one embodiment, a metal barrier is placed over the septum before sterilization of the vial (using, e.g., heat or radiation) to serve as a barrier during final sterilization steps using ethylene oxide or gases, preventing the gases from penetrating the septum.

Following assembly and sterilization of the vial, the vial may be filled with liquid drug in a standard aseptic fill and finish line. For that purpose, the glass vial may be oriented vertically, with its back-end (where the piston is) at the bottom, and filled through the front opening. After the filling step, the front-end of the vial is sealed, e.g., by placing a silicone septum in the opening and crimping a metal ring cap to hold the septum in place. Finally, the vial assembly may be enclosed in an injection-molded protective housing, which may optionally have an adhesive on its underside. The housing may have separate front and back portions (shown in FIG. 7B), which may be connected by a clip-mechanism. The front portion of the housing may include a needle to pierce the drug vial's septum at time of use, and a cannula including a flow sensor and check valve for one-way flow.

Assembling the device (e.g., adding the pump chamber and outer casing), packaging the device in an outer sterile barrier, and boxing it for shipping may be performed with non-sterile techniques, before a final sterilization is used to sterilize the rest of the pump (including the outer areas of the drug vial). This outer sterilization is particularly important for any surfaces that are in contact with the drug. Post-sterilization processes such as treatment with ethylene-oxide gas or gas plasma, e-beam treatment, steam autoclaving, radiation treatment, chemical treatment, or dry heat treatment can all be used. In one embodiment, the resulting drug device has a pump with a sterile drug vial that has an aluminum barrier over its pierceable silicone septum, and a loading needle that can be mechanically driven through the vial's septum and the metal barrier into the drug reservoir, which simultaneously activates the electronics and primes the pump.

Precisely controlled piston pump devices as described herein may be advantageous over traditional body-adhered syringe systems, for example, because they can supply a larger overall volume of drug to a patient while reducing the flow rate from a rapid injection rate to a slower rate of infusion over time. Due to the lower flow rate, a smaller needle may be used to deliver the drug to the patient, resulting in less pain to the patient. Further, in comparison with conventional, manually operated pen injectors, electrolytically driven pump devices in accordance herewith provide greater accuracy and precision in drug dosage, thus increasing patient safety and treatment efficacy.

2. Diaphragm Pump Devices

Figure 11A:
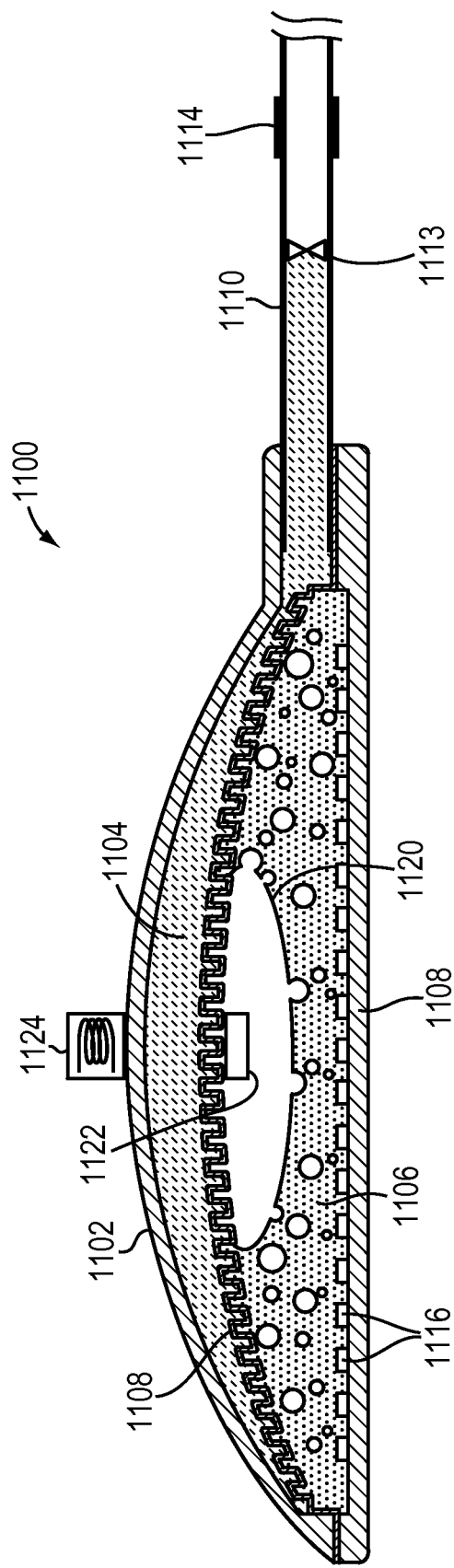
FIGS. 11A and 11B are side and perspective views, respectively, of a diaphragm drug pump device in accordance with one embodiment.
Figure 11B:
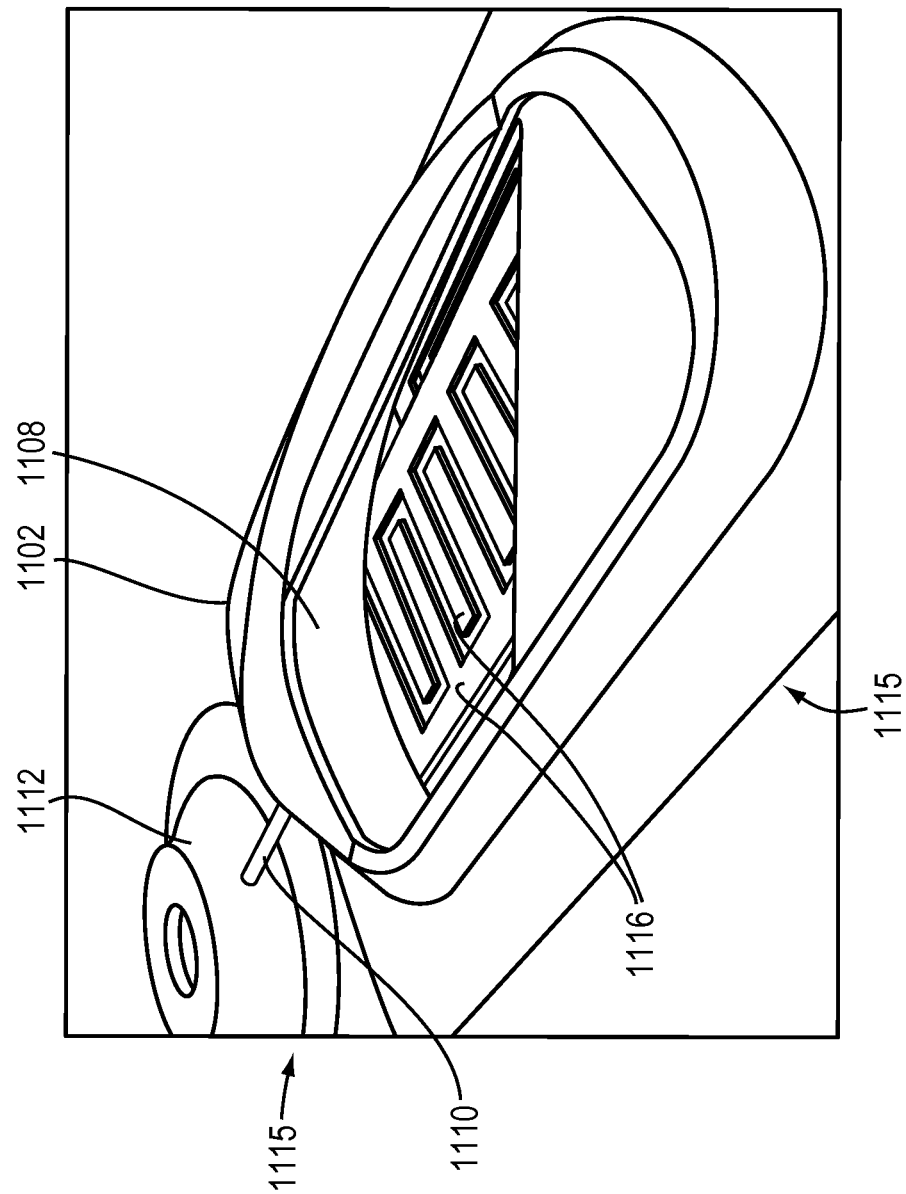

FIGS. 11A and 11B illustrate an exemplary diaphragm pump device 1100 in cross-sectional and perspective views. The device 1100 contains, within a housing 1102 (which is partially removed in FIG. 11B for illustrative purposes only), a drug reservoir 1104 and an electrolysis pump. The pump includes an electrolyte-filled pump chamber 1106 formed between a lower portion of the housing 1100 and a diaphragm 1108. The reservoir 1104 is located on the other side of the diaphragm 1108, above the electrolysis chamber 1106, and is enclosed by the diaphragm 1108 and an upper, typically dome-shaped portion of the housing 1102. The reservoir 1104 may include a refill port that allows for the introduction of additional drug. In some embodiments, the reservoir 1104 is capable of holding between approximately one and ten mL of a drug and has an active operational lifetime of, e.g., between 30 minutes and 75 hours. The capacity and operational lifetime of the reservoir drug pump can easily be adjusted by altering the size of the reservoir 1104 and the rate at which the drug is administered.

The drug reservoir 1104 opens into a cannula 1110, which conducts liquid drug to an infusion set 1112 (not shown in FIG. 11A). The cannula 1110 may contain a check valve 1113 to prevent blood or interstitial fluid from entering the reservoir 1104 and spoiling the drug, as well as a flow sensor 1114 for monitoring the rate at which drug flows to the infusion set 1112. In some embodiments, the infusion set 1112 is detachable from the drug pump device 1100, allowing the infusion set 1112 to stay in place at the infusion site (e.g., with the cannula inserted into the patient's subcutaneous tissue) while the drug device 1100 is removed for refilling or other purposes. Conversely, the pump can remain attached to the patient when the infusion needle or catheter is exchanged (which typically happens every few days). As illustrated in FIG. 11B, the drug pump device 1100 and infusion set 1112 may be mounted on two respective adhesive patches 1115 to be placed in contact with the patient's skin.

A series of low-profile electrolysis electrodes 1116 are disposed at the bottom of the electrolysis chamber 1106. The pump control system may be disposed below the electrodes 1116, e.g., embedded in the lower housing portion 1102. As shown in FIG. 11B, the electrodes 1116 may form interdigitated comb-like structures—a configuration that is advantages because it maximizes the opposing electrode surface area and minimizes the distance between the opposing electrodes, resulting in high electric field strengths in the interjacent space. The electrodes 1116 are generally made of a suitable metal, such as platinum, titanium, gold, or copper, among others.

In operation, when current is supplied to the electrolysis electrodes 1116, the electrolyte filling the pump chamber 1106 evolves gas 1120, expanding the diaphragm 1108 and moving it upwards, i.e., towards the upper portion of the housing 1102. As a result, liquid is displaced from the drug reservoir 1104 and forced into and through the cannula 1110 to a delivery vehicle that is part of the infusion set 1112. The diaphragm 1108 may be corrugated or otherwise folded to permit a large degree of expansion without sacrificing volume within the drug reservoir 1104 when the diaphragm 1108 is relaxed. However, flat or bellows diaphragms may also be used. The diaphragm 1108 may be molded or microfabricated from, for example, parylene polymer. When the current is stopped, the electrolyte gas 1120 condenses back into its liquid state, and the diaphragm 1108 recovers its space-efficient corrugations. The electrolysis pump may be smaller and more portable than other pumps because of its lack of rigidly moving parts, and may be capable of generating high pressures (e.g., greater than 20 psi), allowing the drug pump device to overcome any biofouling or blockages in the system.

The pump 1100 may include a magnet 1120 attached to the underside or the diaphragm 1108. As the magnet 1120 approaches the top of the drug dome 1102, a sensor 1124 determines the relative distance between the magnet and the top of the drug dome, thus indicating when the pump is, e.g., 80%, 90% and 100% empty. The sensor 1124 may, for example, be a magnetic induction coil or a Hall effect sensor. In one embodiment, the pump device alerts (e.g., by means of LED flashes and/or an audio alert, or by wirelessly signaling, for example, a smartphone) the patient when the pump is almost empty (e.g., 80% to 90% empty), and again when the pump is completely empty.

Figure 12A:
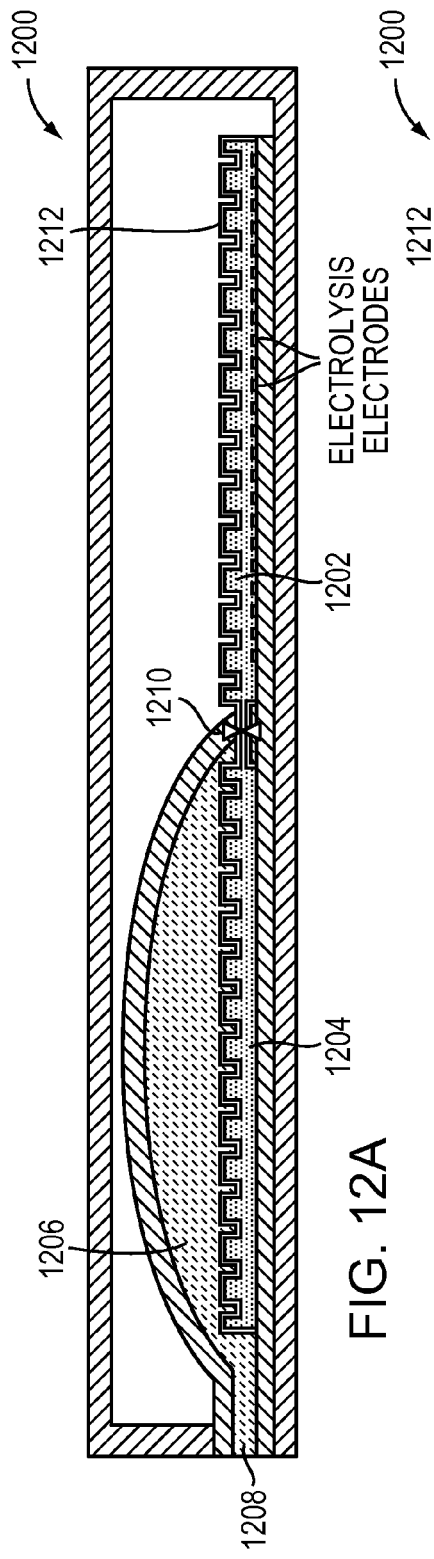
FIGS. 12A-12C are side views of a diaphragm drug pump device with a secondary pump chamber in accordance with one embodiment.
Figure 12B:
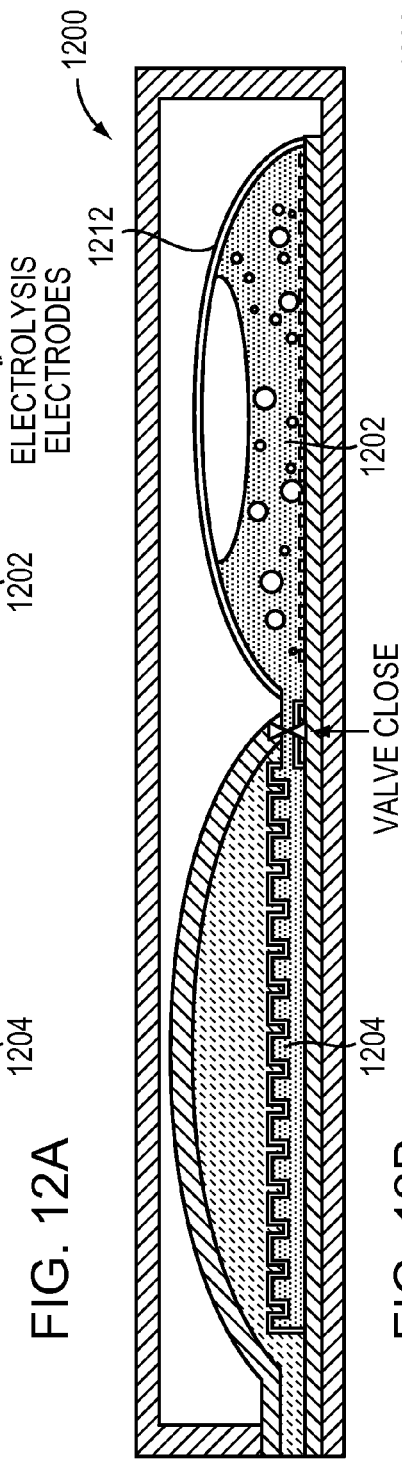
Figure 12C:
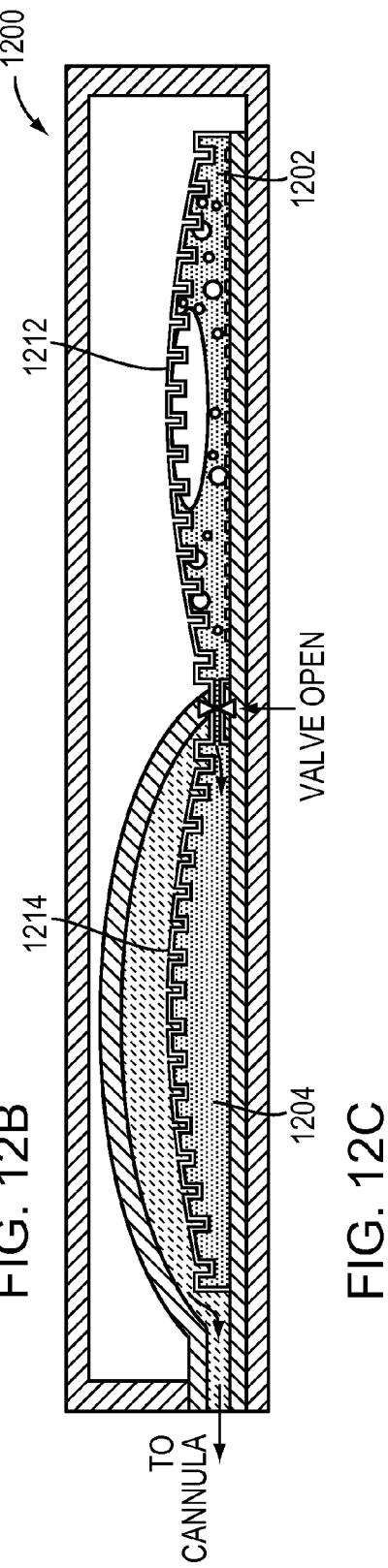

FIGS. 12A-12C illustrate another embodiment of a diaphragm pump device in accordance herewith. The device 1200 includes an electrolysis chamber 1202, a secondary pump chamber 1204 adjacent the electrolysis chamber 1202, and a drug reservoir 1206 disposed above the secondary pump chamber 1204 and opening into a cannula 1208. The electrolysis chamber 1202 and secondary pump chamber 1204 are connected via a fluid path that may be closed by a manually controlled pressure-release valve 1210. This valve 1210 is closed when the electrolysis pump is active, allowing gas to evolve and pressure to build up inside the electrolysis chamber 1202, as shown in FIG. 12B. At least a portion of the enclosure of the electrolysis chamber 1202—as illustrated, the corrugated diaphragm 1212—has strong elastic properties. Therefore, when the electrolysis pump is subsequently turned off and the valve to the secondary chamber is opened, recoil of the elastic enclosure 1212 forces fluid from the pressurized electrolysis chamber 1202 into the secondary pump chamber 1204. As a result, a diaphragm 1214 separating the secondary pump chamber 1204 from the drug reservoir 1206 expands, expelling drug from the reservoir 1206. A pressure sensor inside the electrolysis chamber 1202 may be used to gauge when the electrolysis pump needs to be turned on again. The pump device 1200 facilitates delivering drug continuously while driving the electrolysis only intermittently, which may allow building up a level of pressure inside the pump chamber greater than that achievable with sustained electrolysis. Consequently, this pump configuration may be particularly useful for fast, high-pressure drug injections.

Mechanical recoil may similarly be exploited for power savings in a drug pump device that includes only a single pump chamber, but primary and secondary drug reservoirs. The pump chamber and primary drug reservoir may be arranged and function substantially like the pump device 1100 shown in FIGS. 11A and 11B. Rather than conducting drug from the primary reservoir directly to the infusion site, however, the drug is pumped into the secondary reservoir contained in a flexible bladder, which results in expansion and pressurization of the bladder. The electrolysis pump may then be turned off, and the pressurized bladder thereupon slowly releases the drug for subcutaneous infusion.

Diaphragm pump devices in accordance herewith may include various pump features described above with respect to piston pump devices. For example, to ensure continuous contact between the electrolysis electrode structure and the electrolyte despite changes in the orientation of the device, the electrolyte may be absorbed within a matrix material that is disposed on top of, or otherwise placed in contact with, the electrode structure. Preferably, the matrix material does not retain electrolysis gas and, therefore, substantially does not expand during electrolysis. This facilitates collapsing the expanded diaphragm to refill the drug reservoir to its original volume. In other embodiments, electrode structures (such as a pair of spring coils or flexible wires) that remain in contact with liquid electrolyte regardless of device orientation may be implemented in the electrolysis pump.

Having described certain embodiments of the invention, it will be apparent to those of ordinary skill in the art that other embodiments incorporating the concepts disclosed herein may be used without departing from the spirit and scope of the invention. For example, various features described with respect to one particular device type and configuration may be implemented in other types of device and alternative device configurations as well. Accordingly, the described embodiments are to be considered in all respects as only illustrative and not restrictive.

What is claimed is:

1. A drug pump device comprising:
    an electrolysis pump chamber formed in an enclosure comprising an expandable portion, generation of gas within the electrolysis pump chamber creating pressure to thereby expand the expandable portion;
    a secondary pump chamber located adjacent the electrolysis pump chamber and connected therewith by a fluid path, an upper surface of the secondary pump chamber being formed by a flexible diaphragm;
    a drug reservoir formed between the flexible diaphragm and a dome disposed thereabove; and
    a valve in the fluid path, the valve having a closed state that prevents fluid communication between the electrolysis and secondary pump chambers, thereby facilitating pressure buildup in the electrolysis pump chamber, and an open state that allows electrolyte liquid communication between the electrolysis and secondary pump chambers so as to facilitate release of pressure from the electrolysis pump chamber to the secondary pump chamber, thereby causing drug to be expelled from the reservoir.

2. The drug pump device of claim 1, wherein the expandable portion of the enclosure of the electrolysis pump chamber comprises a flexible diaphragm.

3. The drug pump device of claim 2, further comprising a pressure sensor inside the electrolysis chamber.

* * * * *